(12) United States Patent
Boehnlein et al.

(10) Patent No.: US 7,581,988 B2
(45) Date of Patent: Sep. 1, 2009

(54) DETACHABLE COUPLING FOR A REMOTE INSPECTION DEVICE

(75) Inventors: Al Boehnlein, Ypsilanti, MI (US); Paul J. Eckhoff, Fenton, MO (US); Brandon Watt, Hartland, MI (US); Tye Newman, Howell, MI (US)

(73) Assignee: Perceptron, Inc., Plymouth, MI (US)

( * ) Notice: Subject to any disclaimer, the term of this patent is extended or adjusted under 35 U.S.C. 154(b) by 0 days.

(21) Appl. No.: 12/157,324

(22) Filed: Jun. 9, 2008

(65) Prior Publication Data

US 2008/0248673 A1    Oct. 9, 2008

Related U.S. Application Data

(63) Continuation of application No. 11/645,276, filed on Dec. 22, 2006, now Pat. No. 7,384,308, and a continuation-in-part of application No. 11/480,329, filed on Jun. 30, 2006.

(60) Provisional application No. 60/848,586, filed on Sep. 29, 2006.

(51) Int. Cl.
    *H01R 9/05* (2006.01)
(52) U.S. Cl. ............................... 439/585; 439/587
(58) Field of Classification Search ......... 439/587–589, 439/585
    See application file for complete search history.

(56) References Cited

U.S. PATENT DOCUMENTS

| | | |
|---|---|---|
| 2,488,065 A | 11/1949 | Peterson |
| 3,296,363 A | 1/1967 | Laudig et al. |
| 3,629,792 A | 12/1971 | Dorrell |
| 4,388,523 A | 6/1983 | Keep |
| 4,461,539 A | 7/1984 | Bailey |
| 4,467,802 A | 8/1984 | Maslanka |
| 4,471,766 A | 9/1984 | Terayama |
| 4,629,277 A | 12/1986 | Boettcher |
| 4,779,130 A | 10/1988 | Yabe |
| 5,010,876 A | 4/1991 | Henley |
| 5,170,775 A | 12/1992 | Tagami |
| 5,275,612 A | 1/1994 | Bales, Jr. |
| 5,433,725 A | 7/1995 | Christian et al. |
| 5,527,261 A | 6/1996 | Monroe et al. |
| 5,651,699 A | 7/1997 | Holliday |
| 5,667,473 A | 9/1997 | Finn et al. |

(Continued)

FOREIGN PATENT DOCUMENTS

DE    G9400329.7    5/1994

(Continued)

*Primary Examiner*—Gary F. Paumen
(74) *Attorney, Agent, or Firm*—Harness, Dickey & Pierce, P.L.C.

(57) ABSTRACT

A remote inspection device is provided for inspecting visually obscured locations. The device is generally comprised of a imager housing and a display housing disposed on opposite ends of a modular, flexible cable. An imaging device and one or more light sources are embedded in the end of the cylindrical imager housing. A display housing is coupled to the other end of the flexible cable and configured to be grasped by a user of the device. A display device supported by the display housing receives a video signal from the imaging device and converts the video signal to a video image. The flexible cable can be removably attached to other components with a detachable coupling.

20 Claims, 19 Drawing Sheets

U.S. PATENT DOCUMENTS

| | | | |
|---|---|---|---|
| 5,752,973 | A | 5/1998 | Kieturakis |
| 5,754,220 | A | 5/1998 | Smalser, Sr. |
| 5,823,702 | A | 10/1998 | Bynum |
| 5,928,137 | A | 7/1999 | Green |
| 5,986,752 | A | 11/1999 | Morito et al. |
| 6,043,842 | A | 3/2000 | Tomasch et al. |
| 6,059,719 | A | 5/2000 | Yamamoto |
| 6,086,528 | A | 7/2000 | Adair |
| 6,091,453 | A | 7/2000 | Coan et al. |
| 6,221,007 | B1 | 4/2001 | Green |
| 6,369,849 | B1 | 4/2002 | Rzyski |
| 6,419,626 | B1 | 7/2002 | Yoon |
| 6,530,807 | B2 | 3/2003 | Rodrigues et al. |
| 6,538,732 | B1 | 3/2003 | Drost et al. |
| 6,599,238 | B2 | 7/2003 | Ooshima et al. |
| 6,664,473 | B2 | 12/2003 | Christman |
| 6,669,511 | B1 | 12/2003 | Yagi |
| 6,875,169 | B2 | 4/2005 | Berci et al. |
| 7,009,698 | B2 | 3/2006 | Drost et al. |
| 7,048,579 | B2 | 5/2006 | Montena |
| 7,156,695 | B2 | 1/2007 | Holliday |
| 7,241,164 | B2 | 7/2007 | Holliday |
| 7,264,503 | B2 | 9/2007 | Montena |
| 7,458,849 | B2 * | 12/2008 | Rodrigues et al. ............ 439/578 |
| 2001/0024910 | A1 | 9/2001 | Ishii et al. |
| 2002/0148633 | A1 | 10/2002 | Kanda |
| 2004/0054254 | A1 | 3/2004 | Miyake |
| 2004/0058575 | A1 | 3/2004 | Nicholson |
| 2004/0097130 | A1 | 5/2004 | Holliday |
| 2004/0110418 | A1 | 6/2004 | Holliday et al. |
| 2004/0193007 | A1 | 9/2004 | Martone et al. |
| 2004/0198095 | A1 | 10/2004 | Laverick |
| 2004/0248466 | A1 | 12/2004 | McCarthy |
| 2005/0048836 | A1 | 3/2005 | Holliday |
| 2006/0200001 | A1 | 9/2006 | Keller |

FOREIGN PATENT DOCUMENTS

| | | |
|---|---|---|
| DE | 10132825 | 1/2001 |
| EP | 0360471 | 3/1990 |
| EP | 1548895 | 6/2005 |
| GB | 780702 | 8/1957 |
| GB | 780703 | 8/1957 |
| GB | 983195 | 2/1965 |
| GB | 1015479 | 12/1965 |
| JP | 63-43277 | 2/1988 |
| JP | 3899159 | 10/1998 |
| JP | 2001-203030 | 7/2001 |
| JP | 2005-326523 | 11/2005 |
| WO | 88-10440 | 12/1988 |
| WO | 95-08200 | 3/1995 |

* cited by examiner

DETACHABLE COUPLING FOR A REMOTE INSPECTION DEVICE

CROSS-REFERENCE TO RELATED APPLICATIONS

This application is a continuation of U.S. patent application Ser. No. 11/645,276 filed on Dec. 22, 2006 which claims the benefit of U.S. patent application No. 60/848,586 filed on Sep. 29, 2006 and is a continuation-in-part of U.S. patent application Ser. No. 11/480,329 filed on Jun. 30, 2006. The disclosures of the above applications are incorporated herein by reference.

FIELD

The present disclosure relates generally to borescopes and video scopes.

BACKGROUND

Borescopes and video scopes for inspecting visually obscured locations are typically tailored for particular applications. For instance, some borescopes have been tailored for use by plumbers to inspect pipes and drains. Likewise, other types of borescopes have been tailored for use by mechanics to inspect interior compartments of machinery being repaired. Special features and functions associated with these applications have driven up the cost for these types of devices. Absent from the marketplace is a simplified, inexpensive and yet versatile inspection device which may be marketed to the general public.

The statements in this section merely provide background information related to the present disclosure and may not constitute prior art.

SUMMARY

The present disclosure provides a detachable coupling for selectively attaching first and second cables of a remote inspection device. The detachable coupling includes a first ferrule component provided over the first cable and having an end cap extending over an end of the first cable. The first ferrule component is an electrical insulator. The detachable coupling further includes a first casing engaging the first ferrule component, the first casing and the first ferrule component being secured to the first cable. The first ferrule component provides a seal to inhibit fluid communication between the first casing and the first cable and electrically isolates the first casing from the first cable. The detachable coupling also includes a first electrical connector supported within the first casing and electrically connected to wires in the first cable. The detachable coupling includes a second ferrule component provided over the second cable and having an end cap extending over an end of the second cable, The second ferrule component is an electrical insulator. The detachable coupling further includes a second casing engaging the second ferrule component, the second casing and the second ferrule component being secured to the second cable. The second ferrule component provides a seal to inhibit fluid communication between the second casing and the second cable and electrically isolates the second casing from the second cable. The detachable coupling also includes a second electrical connector supported within the second casing and electrically connected to wires in the second cable. The first and second casings engage and inhibit relative rotation therebetween, and the first and second electrical connectors engage and electrically connect the wires of the first and second cables.

The present disclosure further provides another detachable coupling for selectively attaching first and second cables of a remote inspection device. The detachable coupling includes a first assembly attached to the first cable and a second assembly attached to the second cable. The first assembly includes a ferrule component provided over the first cable. The ferrule component has a generally cylindrical main body and an end cap extending over an end of the first cable. The ferrule component further has at least one protrusion extending from an outer surface of the main body. The ferrule component is an electrical insulator and is deformable. The first assembly further includes a casing engaging and deforming the ferrule component. The casing has a generally cylindrical portion extending over the ferrule component. The cylindrical portion has an inside surface with at least one recess complementary to the at least one protrusion. The at least one protrusion and the at least one recess engage to inhibit relative axial movement between the ferrule component and the casing. The ferrule component and the casing are secured to the first cable. The ferrule component provides a seal to inhibit fluid communication between the casing and the first cable and electrically isolates the casing from the first cable. The first assembly also includes an electrical connector supported within the casing and electrically connected to wires in the first cable. The first and second assemblies selectively engage so as to inhibit relative rotation therebetween and to electrically connect the wires in the first cable to wires in the second cable.

The present disclosure further provides a remote inspection device. The remote inspection device includes an imager housing including an imaging device, a display housing including a display device and a portable power source, and a first cable having a first end coupled to the imager housing and a second end coupled to the display housing. The first cable has a plurality of wires and an outer jacket. The wires operably connect the portable power source and the imaging device. The wires further operably connect the imaging device and the display device. The remote inspection device further includes a detachable coupling connecting the first cable and the imager housing. The detachable coupling includes a first assembly fixed to the first end said first cable and a second assembly coupled to the imager housing. The first assembly includes a first ferrule component provided over the first cable and having an end cap extending over the first end of the first cable. The first ferrule component is an electrical insulator. The first assembly further includes a first casing engaging the first ferrule component, the first casing and the first ferrule component being secured to the first cable. The first ferrule component provides a seal to inhibit fluid communication between the first casing and the first cable and electrically isolates the first casing from the first cable. The first assembly also includes a first electrical connector supported within the first casing and electrically connected to the wires.

The present disclosure further provides a method of assembling a detachable coupling for a remote inspection device. The method includes providing a first ferrule component on a first cable and disposing a first casing over the first ferrule component and the first cable. The method further includes deforming the first ferrule component with the first casing, the first ferrule component providing a seal between the first casing and the first cable to inhibit fluid communication therebetween. The method also includes supporting a first electrical connector in the first casing, electrically connecting wires in the first cable and the first electrical connector, filling a space within the first casing between the first cable and the first electrical component with an insulating material, and mating the first casing and the first electrical connector with a complementary assembly attached to a second cable, the first and second cables being mechanically and electrically connected.

Further areas of applicability will become apparent from the description provided herein. It should be understood that the description and specific examples are intended for purposes of illustration only and are not intended to limit the scope of the present disclosure.

DRAWINGS

Figure 1:
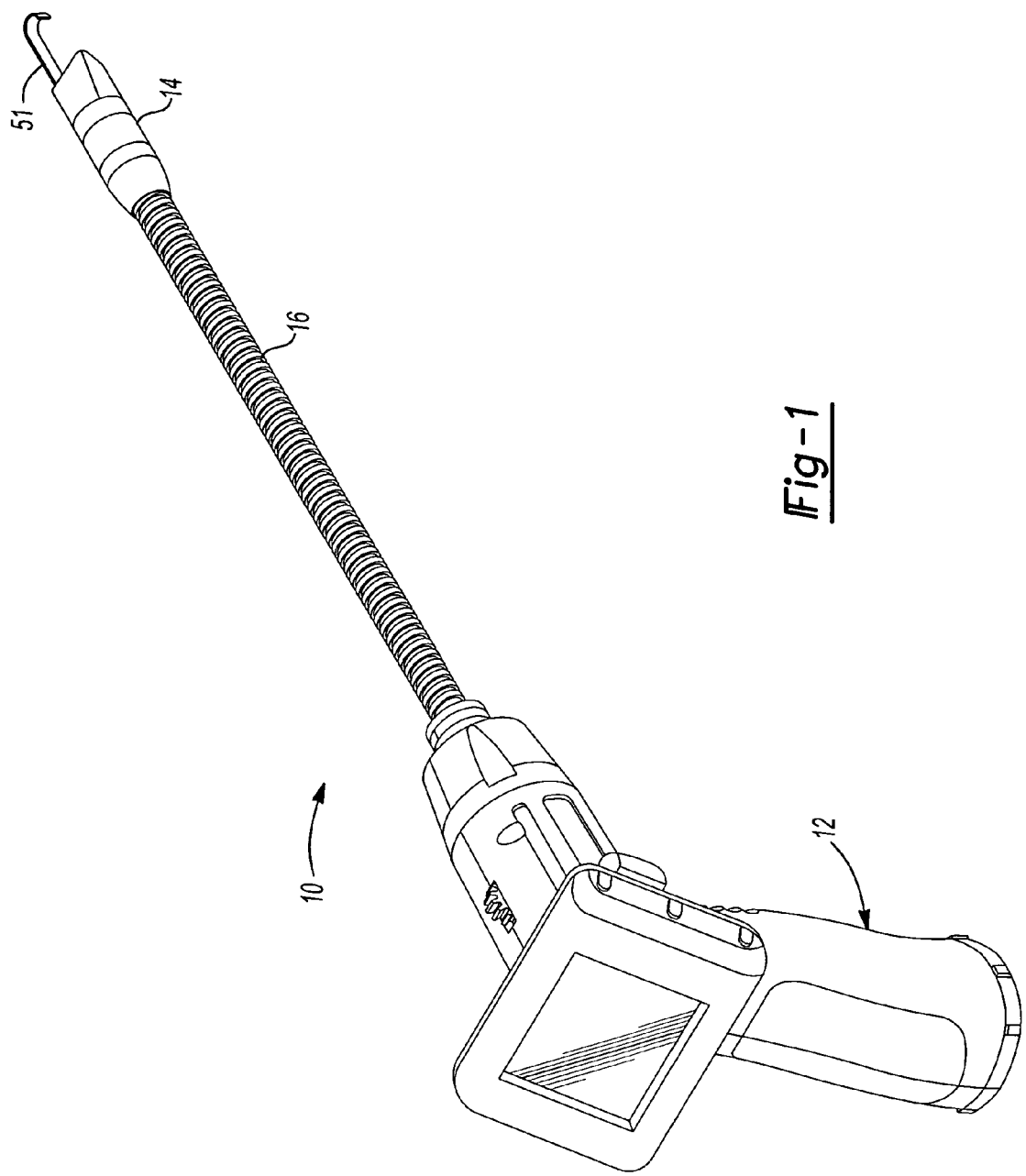
FIG. 1 is a perspective view of an exemplary inspection device.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

FIG. 1 illustrates an exemplary embodiment of a remote inspection device 10. The remote inspection device 10 is generally comprised of three primary components: a display housing 12, an imager housing 14 and a flexible cable 16 interconnecting the display housing 12 to the imager housing 14. The flexible cable 16 may be bent or curved as it is pushed into visually obscured areas, such as pipes, walls, etc. In an exemplary embodiment, the flexible cable 16 is a ribbed cylindrical conduit having an outer diameter in the range of 1 cm. The conduit can be made of either a metal, plastic or composite material. Smaller or larger diameters may be suitable depending on the application. Likewise, other suitable constructions for the flexible cable 16 are also contemplated by this disclosure.

The imager housing 14 is coupled to a distal end of the flexible cable 16. In the exemplary embodiment, the imager housing 14 is a substantially cylindrical shape that is concentrically aligned with the flexible cable 16. However, it is envisioned that the imager housing 14 may take other shapes. In any case, an outer diameter of the cylindrical imager housing 14 is preferably sized to be substantially equal to or greater than the outer diameter of the flexible cable 16.

Figure 2A:
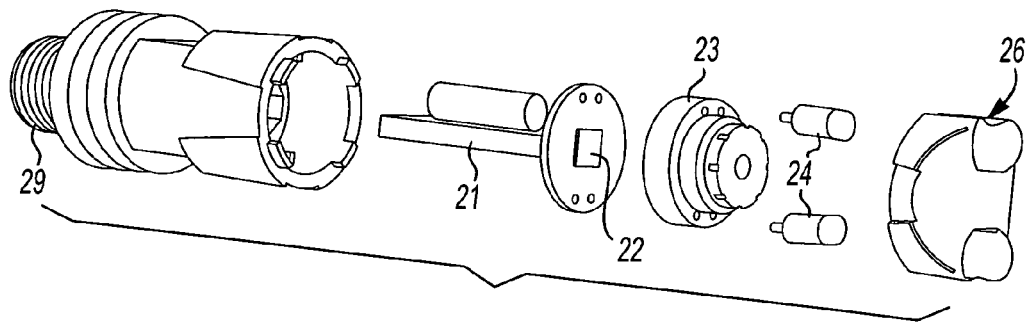
FIGS. 2A and 2B are exploded views of exemplary imager housings of the inspection device.

With reference to FIG. 2A, the imager housing 14 is configured to house an imaging device 22 and one or more light sources 24. The imaging device 22 is embedded in an outwardly facing end of the imager housing. In particular, the imaging device 22 is coupled to an end of a circuit board 21 which in turn slides into an internal cavity of the imager housing 14. The imaging device 22 is operable to capture an image of a viewing area proximate to the outwardly facing end of the imager housing 14. The imaging device 22 may be implemented using a charge-coupled device (CCD), a CMOS-based image sensor, a digital image sensor, or other types of commercially available imaging devices. Image data is focused onto the imaging device 22 by a lens assembly 23 positioned adjacent to the imaging device 22.

Figure 3:
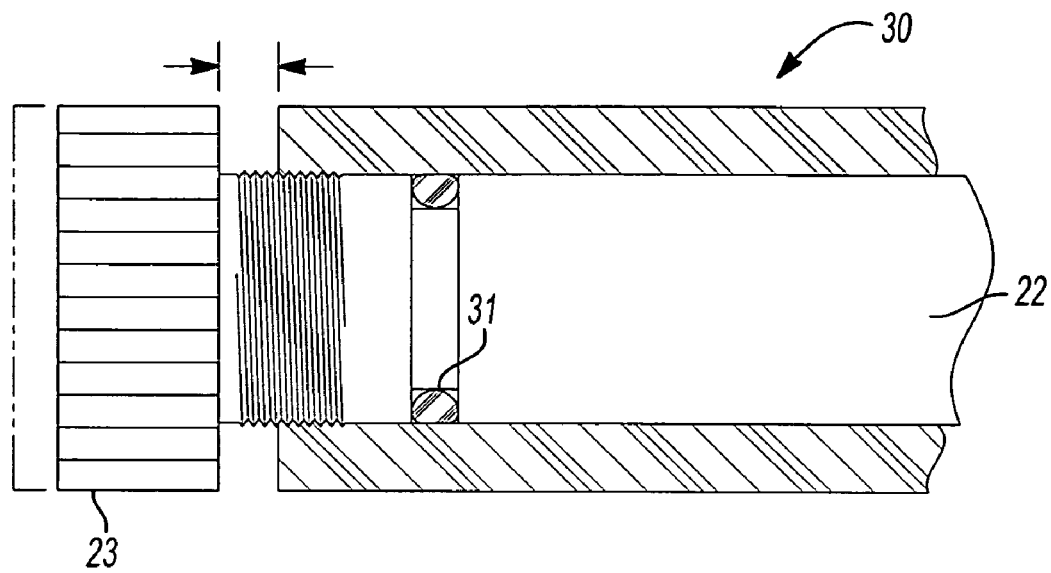
FIG. 3 is a cross-sectional view of a imager housing having a sealable user adjustable focus mechanism.

In the exemplary embodiment, the imaging device 22 and lens assembly 23 provides a fixed focus at approximately four to ten inches from the end of the imager housing. However, it is envisioned that the inspection device 10 may provide an adjustable focus. For instance, a user adjusted focus mechanism 30 is shown in FIG. 3. Through a fine mechanical screw thread or any similar movement device, the lens assembly 23 can be moved axially nearer or farther from the imager 22. This movement changes the focus of the imaging device. At the same time, a seal 31 must be provided to prevent foreign materials from entering the mechanism. In another instance, the imaging device and lens assembly may be replaced with an auto-focus camera module. In this instance, a more sophisticated processor and drive motor assembly is needed to drive the camera module.

Figure 2B:
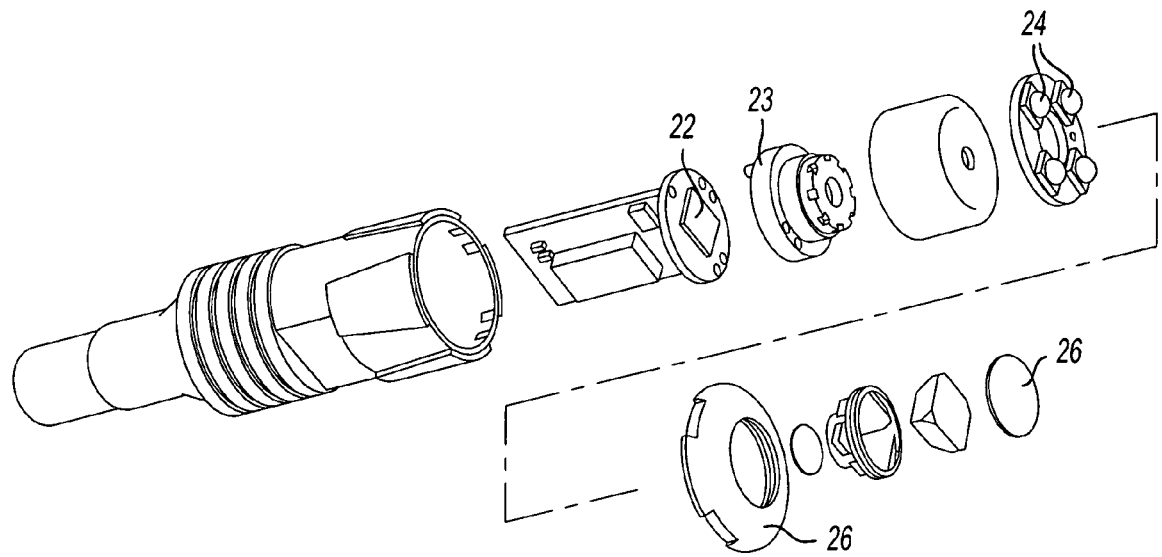
Figure 2C:
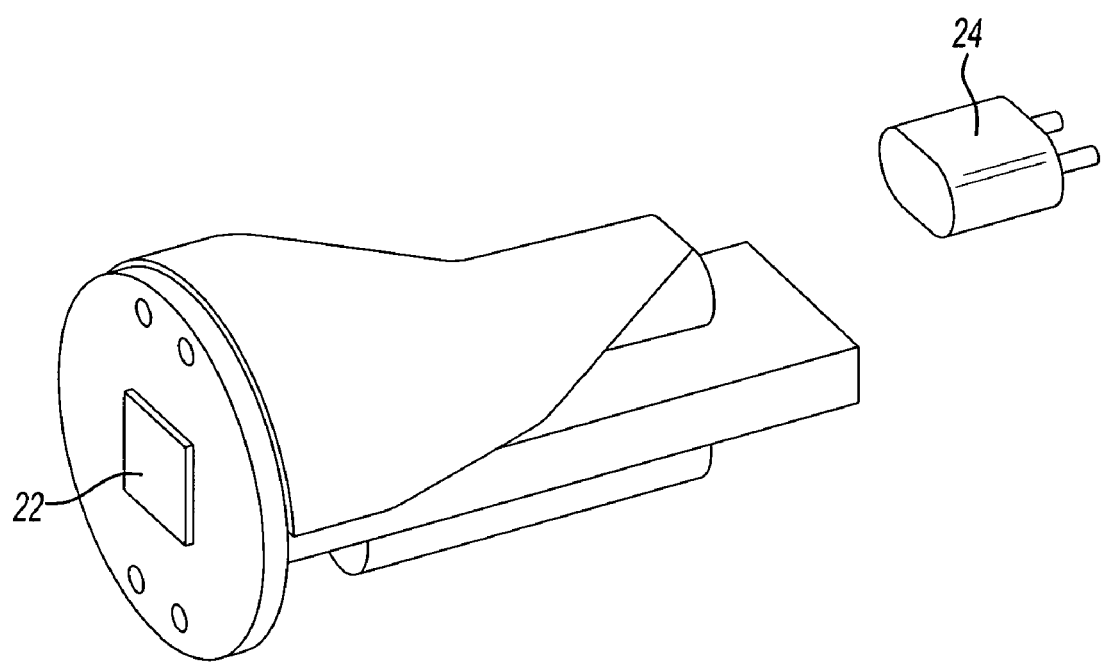
FIG. 2C is a diagram depicting an exemplary piping structure for guiding light through the imager housing.
Figure 4:
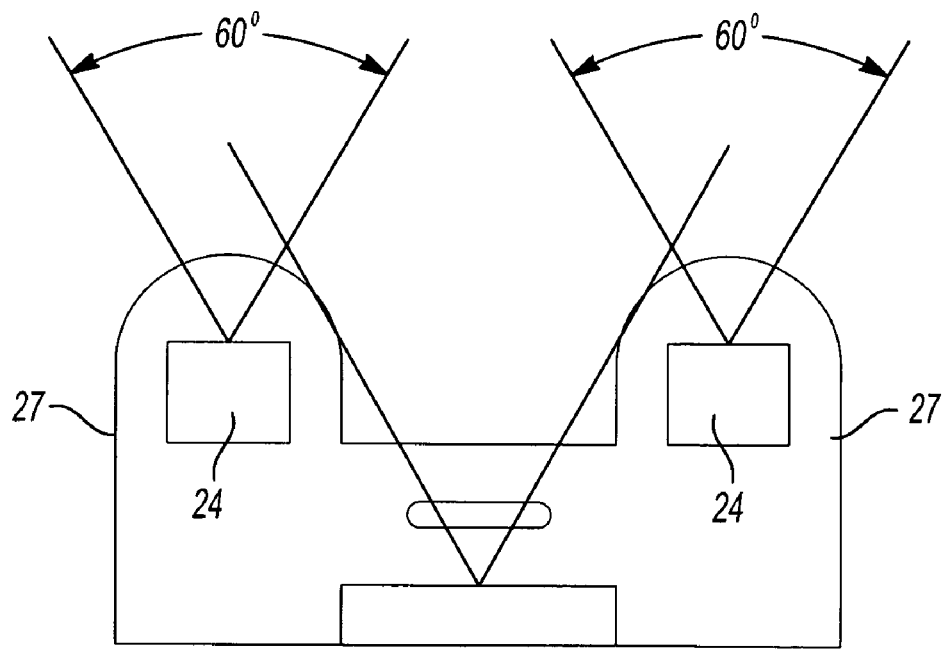
FIG. 4 is a cross-sectional schematic view of the imager housing.

With continued reference to FIG. 2A, one or more light sources 24 for illuminating the viewing area are also electrically connected to the circuit board 21. In the exemplary embodiment, two light emitting diodes (LEDs) are disposed along the perimeter of the imaging device 22. The LEDs protrude outwardly from the circuit board such that the imaging device 22 and lens assembly 23 is recessed between the two LEDs as shown in FIG. 4. The LEDs may optionally be connected to a separate circuit board residing in the camera head. Alternatively, the LEDs 24 may be recessed behind the imaging device 22 and/or lens assembly, such that light from the LEDs is transferred or piped to an emitting point which extends above and beyond the imaging device 22. An exemplary piping structure is shown in FIG. 2C. In either instance, recessing the imaging device and lens assembly behind the light emitting point reduces the amount of backscattered or interfering light from the LEDs.

A transparent cap 26 encloses these components within the imager housing 14. For instance, the cap 26 may be made of an acrylic material that enables light to project from the LEDs into the viewing area and return from the viewing area to the imaging device. Other types of durable transparent material may be used in place of acrylic. In the exemplary embodiment, each of the protruding LEDs is encased by a nipple 27 formed in the cap 26. To sufficiently illuminate the viewing area, each LED should preferably project light proximate to the view angle of the imager at a 60 degree view angle away from the image housing 14. LEDs having such a view angle may be used. However, LED's having a 132 degree view angle provide a more inexpensive alternative. In this case, the ends of the nipples 27 may be curved to form a lens which focuses the light from the LEDs to a 60 degree view angle as shown in FIG. 4. Thus, the cap 26 may also serve as a lens for the light sources. The cap 26 is preferably ultrasonically welded to the outwardly facing end of the imager housing 14, thereby creating a sealed enclosure; otherwise, techniques for sealing the cap to the imager housing are also contemplated. An alternative embodiment for the imager housing 14 is shown in FIG. 2B.

In one exemplary embodiment, the imager housing 14 couples to the flexible cable 16 by way of a threaded sleeve 29 integrally formed at one end of the imager housing 14. The threaded sleeve 29 on the imager housing screws into a grooved portion from along an interior surface of a coupling formed on the distal end of the flexible cable. The sleeve and coupling each provide an axial passageway for a plurality of wires that are electrically connected between the circuit board in the imager housing and the display housing. The plurality of wires may or may not be further encased in a protective cable.

Figure 5A:
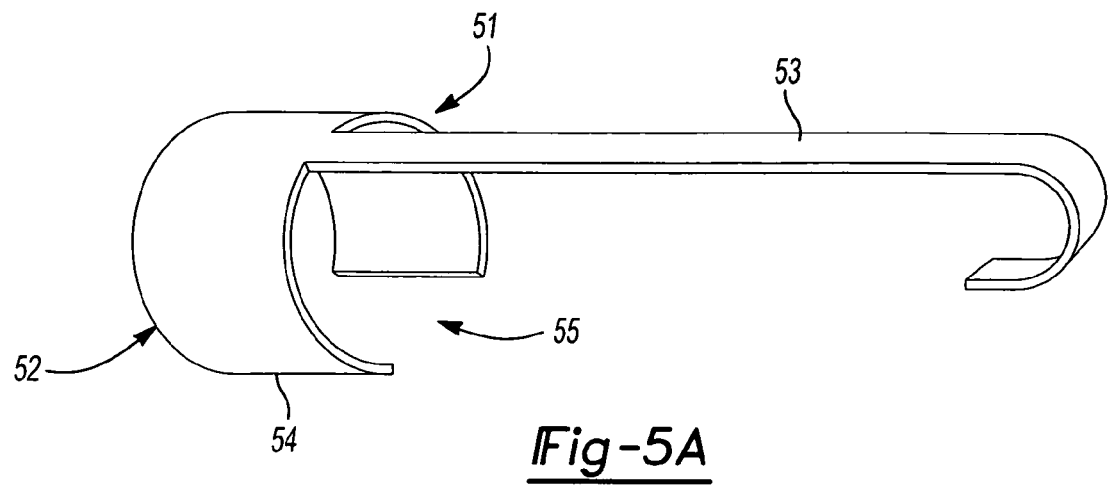
FIGS. 5A-5C are perspective views of exemplary attachments for the imager housing.
Figure 5B:
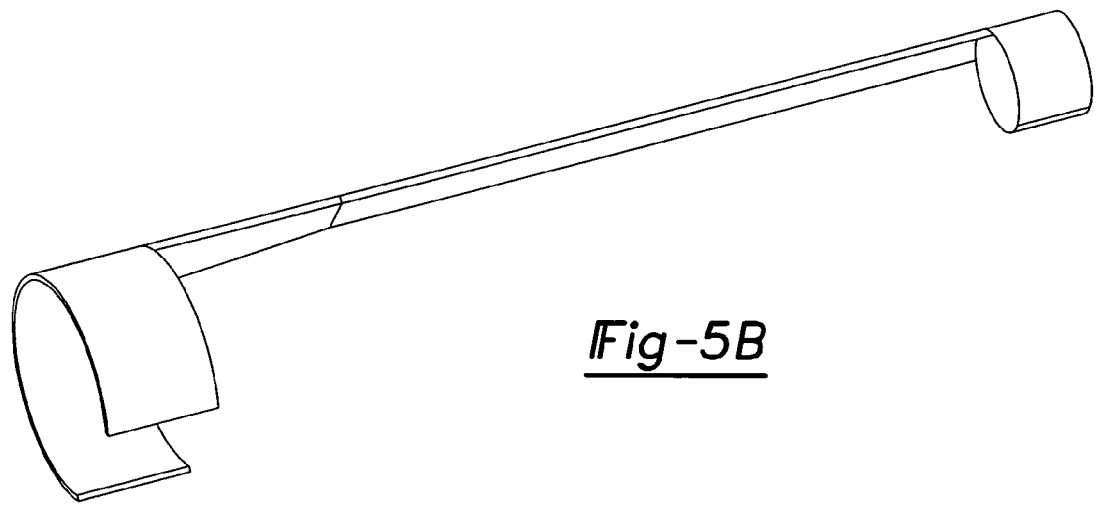
Figure 5C:
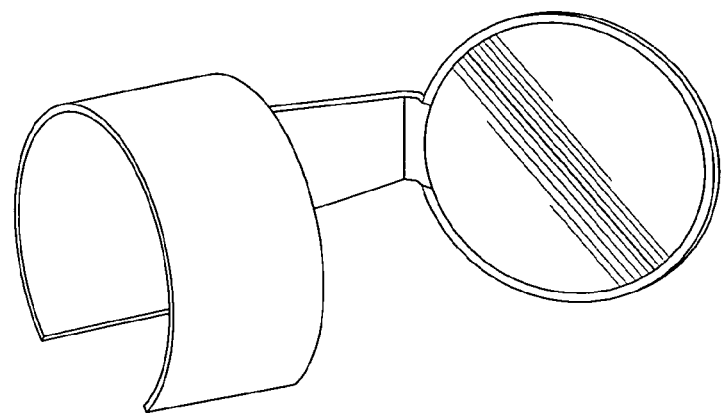

With reference to FIGS. 5A-5C, an attachment 51 may be removably coupled to the imager housing 14. The attachment 51 is generally comprised of a finger portion 53 which extends in parallel to the axis of the cylindrical imager housing and beyond an outwardly facing end of the housing, and a clip 52 that attaches to the cylindrical housing. A distal end of the finger portion 53 may be further configured to retrieve or otherwise manipulate objects proximate to the end of the imager housing 14. For instance, the attachment 51 may be configured with a hook as shown in FIG. 5A or with a magnet as shown in FIG. 5B. In another instance, the attachment may be a mirror as shown in FIG. 5C. Other configurations, such as a loop, lance, or cutting device, are also contemplated by this disclosure.

Figure 6A:
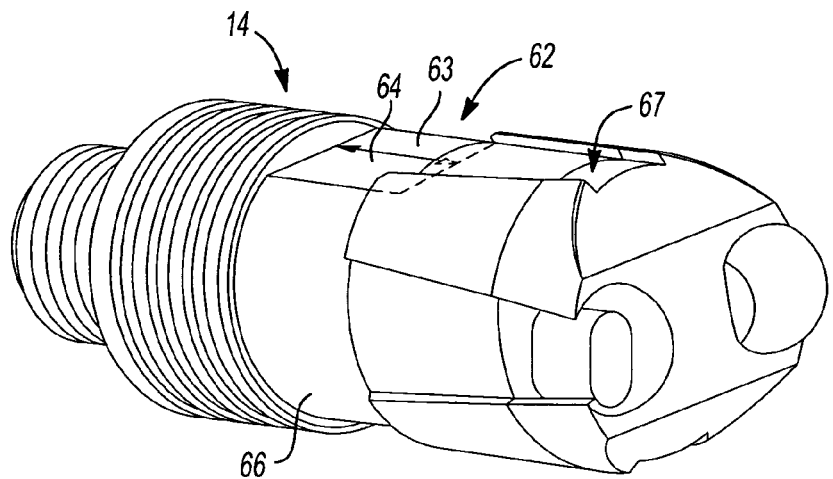
FIG. 6A is a perspective view illustrating the engagement area for an exemplary attachment on the imager housing.

In an exemplary embodiment, the imager housing provides an engagement area for the attachment 51 as shown in FIG. 6A. The engagement area is comprised of an annular recess 62 formed in the outer surface of the imager housing. Within the annular recess, two opposing cutaways 62 are also formed, where each cutaway 62 defines a recessed rectangular planar surface 63 having a longitudinal axis 64 in parallel with the axis of the cylindrical imager housing. A radial surface 66 is formed between the two opposing cutaways. The clip 52 is further defined as a cylindrical band 54 having a radial gap 55 formed therein, such that the radial gap 55 of the clip 52 is slightly larger than the remaining radial surface 66. In addition, the annular recess 62 is sized to receive the cylindrical band 54 of the clip. The engagement area may further include a locking groove 67 formed in the radial surface thereof and extends in parallel to the axis of the cylindrical imager housing. The locking groove 67 is sized to receive the finger portion 53 of the attachment.

Figure 6B:
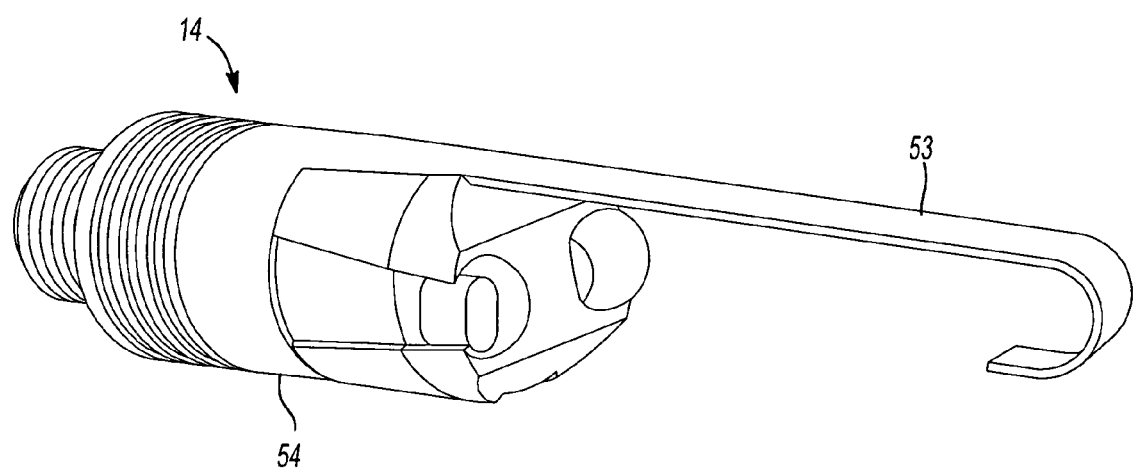
FIG. 6B is a perspective view illustrating an exemplary attachment coupled to the imager housing.
Figure 6C:
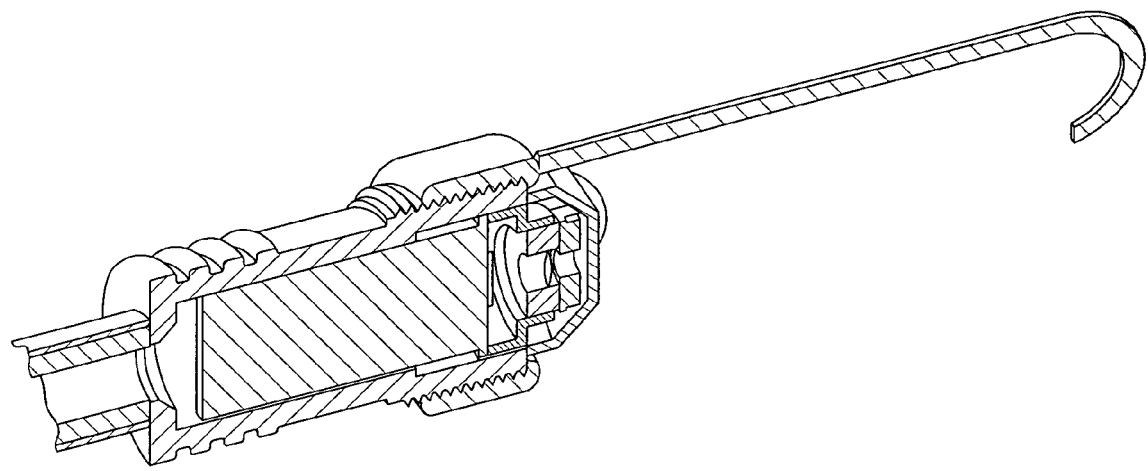
FIG. 6C is a perspective view illustrating an alternative coupling means for attaching an attachment to the imager housing.

Referring to FIG. 6B, the attachment 51 is coupled to the imager housing 14 by sliding the cylindrical band 54 over the recessed portion of the housing 14 and into the annular recess 62. Recessed into the annular recess prevent the attachment from sliding forward or backwards along the imaging housing. The attachment 51 is then rotated 90 degrees around the axis of the housing until the finger portion 53 of the attachment 51 is recessed into the locking groove, thereby preventing attachment 51 from rotating about. The spring load of the band pulls the finger portion into the locking groove 67 to further prevent detachment from the imager housing. It is understood that the clip mechanism is a non-limiting example of how the attachment may be removably coupled to the imager housing. FIG. 6C illustrates a threaded coupling between the attachment 51 and the imager housing 14. Other coupling means, such as magnetic, are also contemplate by this disclosure.

Figure 7:
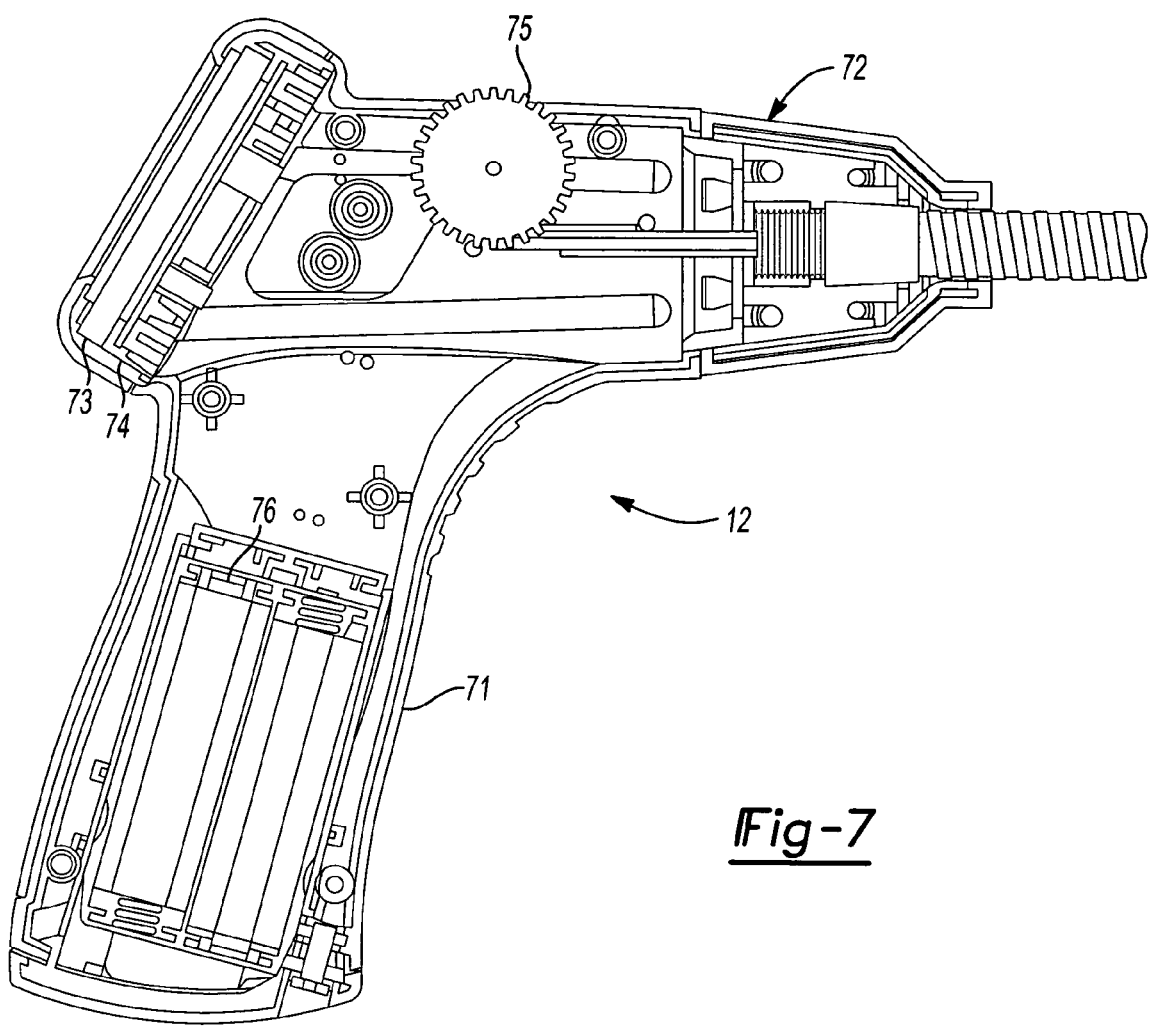
FIG. 7 is a cross-sectional view of an exemplary display housing.

Referring to FIG. 7, the display housing 12 is coupled to a proximate end of the flexible cable 16. In an exemplary embodiment, the display housing 12 is in the shape of a pistol. Specifically, the display housing 12 includes a handle portion 71 configured to be grasped by an operator of the device and a protruding portion 72 extending away from the user when grasped by the user, such that the protruding portion forms an obtuse angle relative to the handle portion of the housing display. Other handheld configurations for the display housing also fall within the broader aspects of this disclosure.

Figure 8A:
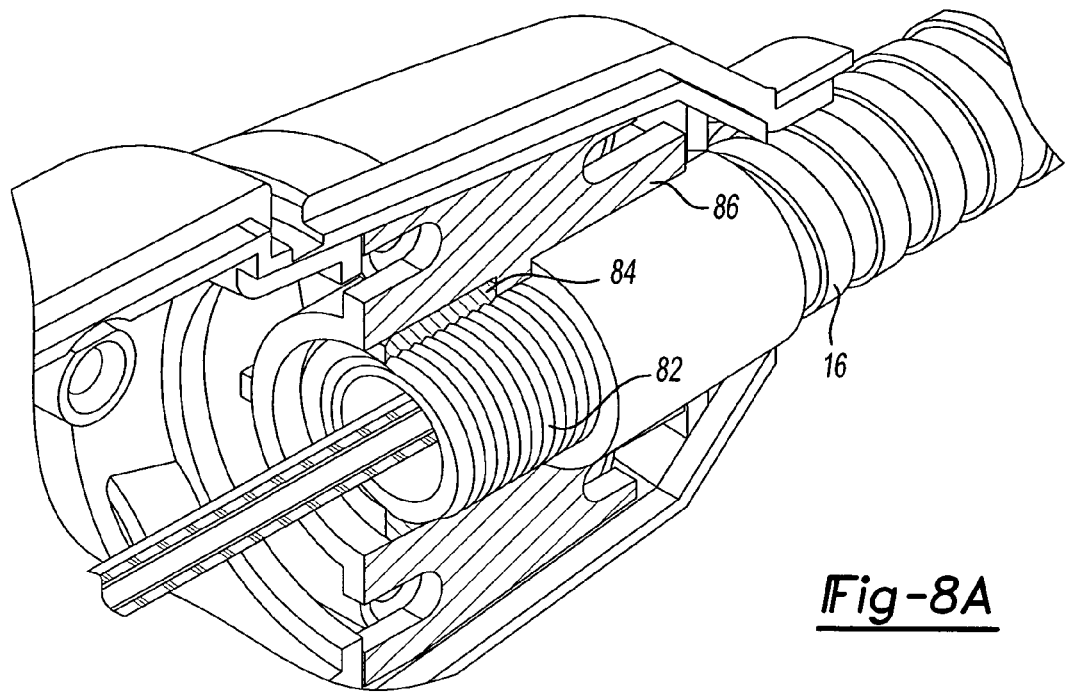
FIGS. 8A and 8B are fragmentary sectional views illustrating the coupling of the flexible cable to the display housing.
Figure 8B:
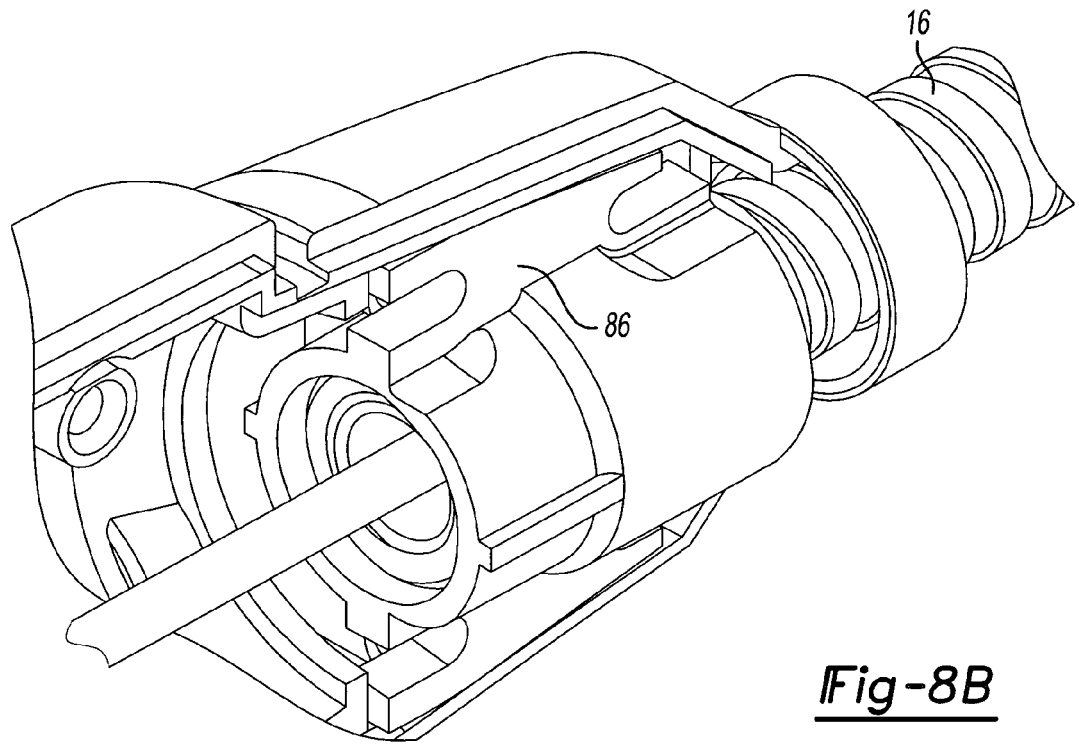

In one exemplary embodiment, a threaded male connector 82 formed on the proximate end of the flexible cable 16 is used to couple the cable to the display housing 12 as best seen in FIGS. 8A and 8B. In this case, a knurled nut 84 is fixed with the nut retainer 86. The male connector 82 is screwed into the knurled nut 84, thereby coupling the flexible cable 16 to the nut retainer 86. The nut retainer is then attached into the protruding portion of the display housing 12. Other types of connections are contemplated by this disclosure.

Returning to FIG. 7, the display housing 12 is configured to support the remaining operational components of the inspection device. In the exemplary embodiment, the operational components include a display device 73, an interface board 74, a power switch 75 and a power source 76 (i.e., 4 AA alkaline batteries). The display device 73 is preferably orientated towards the operator as the operator grasps the handle portion 71 of the device. Although a liquid crystal display is presently preferred, it is understood that other types of display devices, such a cathode ray tube or a LED display, may also be used.

Figure 9:
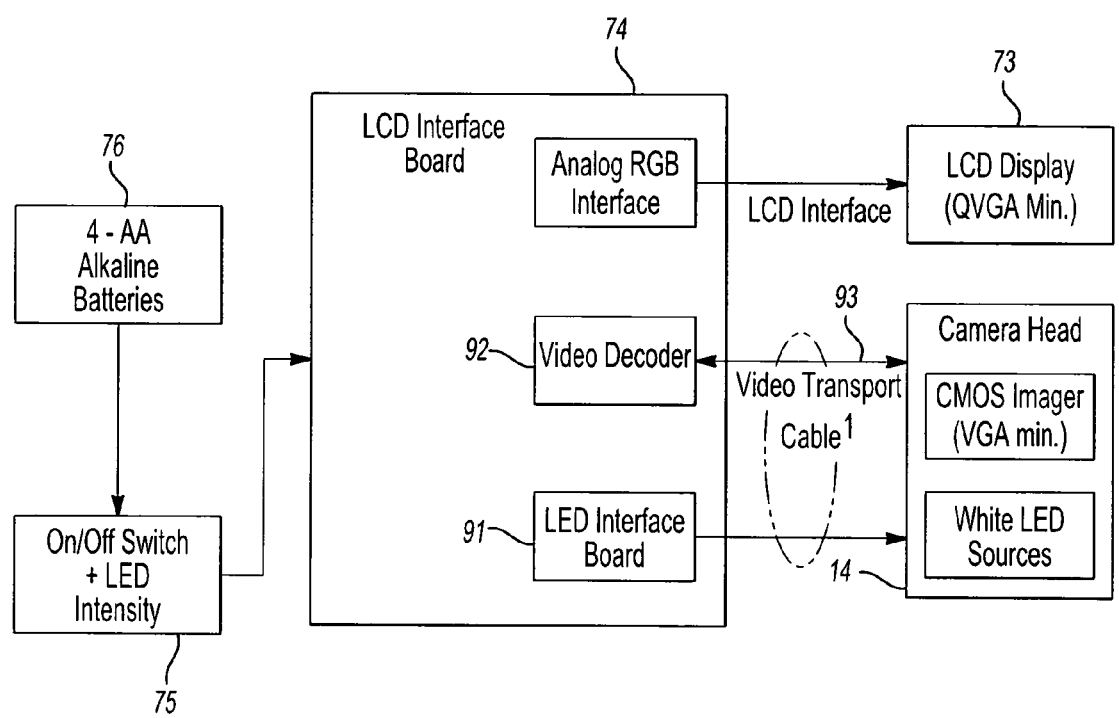
FIG. 9 is a block diagram of the operational components which comprise the inspection device.

Operational aspects of the inspection device are better understood from a schematic provided in FIG. 9. The power switch 75 is interposed between the power source 76 and the remaining operational components. When actuated by an operator to an ON position, power is supplied from the power source 76 to the interface board 74. The interface board 74 in turn powers the display device 73 and the imaging device 22.

In the exemplary embodiment, the power switch 75 is further operable to control the intensity of the LEDs. To do so, power is also supplied to an LED interface board 91. The LED interface board 91 in turn sends a control signal to the LEDs based on the setting of the power switch 75. As the dial is rotated further away from an ON position, the intensity of the LEDs is increased. In this way, the operator can adjust the illumination of the viewing area, thereby improving the quality of the acquired images. Alternative embodiments of the inspection device may employ other user actuated controls. For example, the inspection device may include controls for the contrast of the display device, on-screen display or for a zoom function of the imaging device.

Once powered on, the imaging device 22 begins capturing images and transmitting the image data as a video signal to a video decoder 92 residing on the interface board 74. The video decoder 92 decodes the video signal and passes it through another interface to the display device 73. The display device 73 is then operable to display the video images to the operator.

In the exemplary embodiment, the imager housing is connected by a four wire twisted pair cable to the display housing. Functions for each wire are specified as follows: a power wire for delivering electrical power to the imaging device, a video wire for transporting the captured image data (e.g., a NTSC signal) from the imager back to the interface board, a control signal for varying the intensity of the light source and a ground connection. It is envisioned that more or less wires may be needed to support different functionality.

In an alternative embodiment, the inspection device may provide an image self-righting feature. As the camera head is pushed into inspection areas, it may get twisted so that the images displayed to the operator are disoriented. To orientate the images, an accelerometer is placed in the imager housing. The accelerometer is operable to report the position of the camera head in relation to a sensed gravity vector. Given the position data and the image data, a microprocessor residing in the display housing can apply a known rotation algorithm (e.g., rotation matrix) to the image data. In this way, the image data is always presented upright to the operator.

Figure 10:
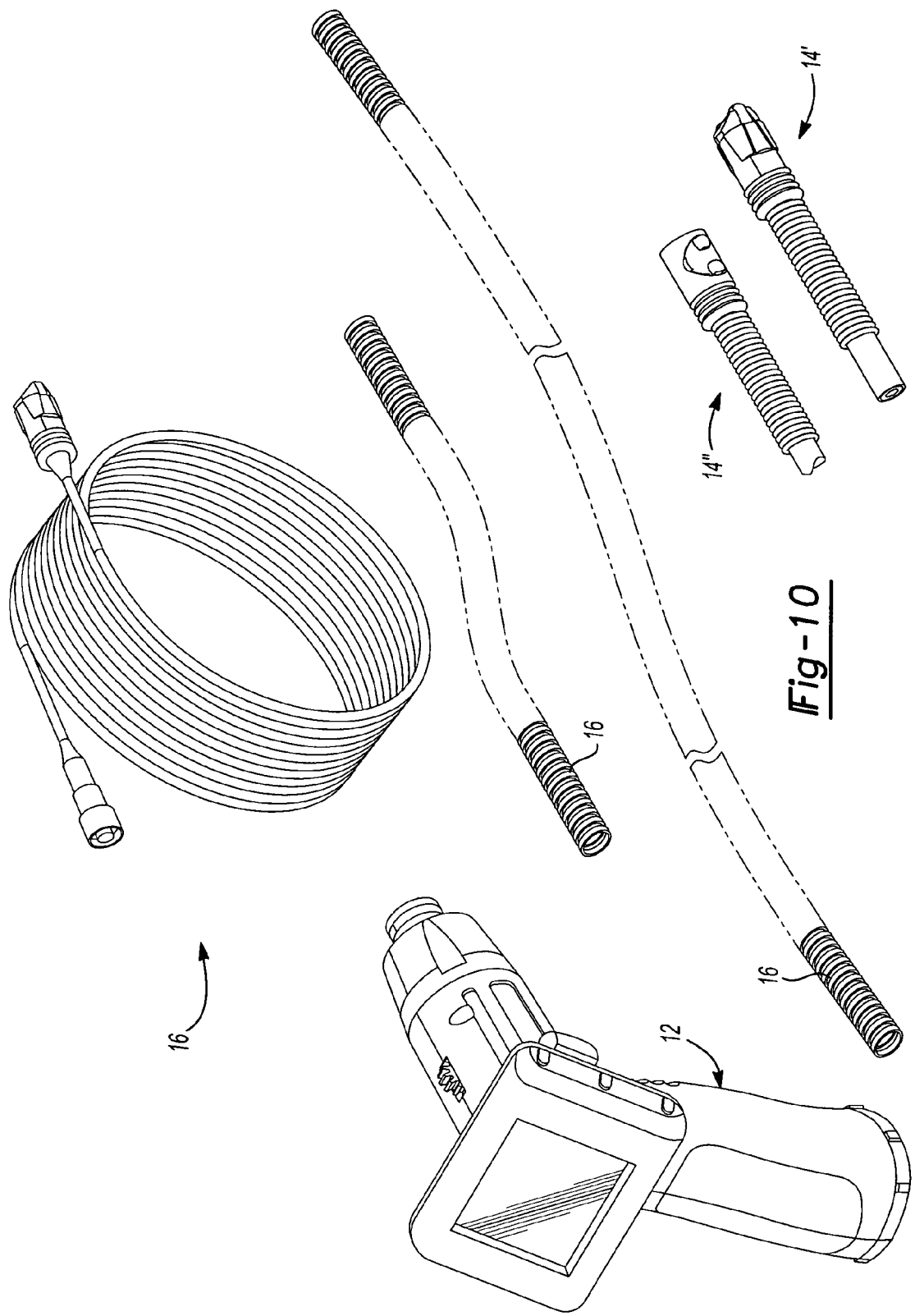
FIG. 10 is a perspective view illustrating a modular design for the inspection device.

In another aspect of this disclosure, the remote inspection device may be designed to be modular as shown in FIG. 10. In general, the more expensive processing components, such that the LCD, are disposed in the display housing; whereas, lesser expensive components are used to construct the imager housing. Modularity enables the lesser expensive components to be interchanged or replaced as needed.

For example, a detachable coupling between the imager housing and the flexible cable enables imager housings of varying sizes to be used with the same display housing. The flexibility allowed by the modularity of this device also allows the cost efficient manufacture of easily replaceable imager heads that could be fixed at any desired spherical orientation in regard to the central axis of the cable or the imager head. A first imager head 14' may be constructed as described above with the imaging device orientated along the central axis of the imager head; whereas, a second imager head 14" provides an imaging device orientated at 90 degrees to the central axis of the imager head. Imager heads have other orientations are also contemplated.

Likewise, a second detachable coupling between the display housing and the flexible cable enables the use of different types of cables while retaining the same imager housing. Depending on the application, cables may vary in length from 3 feet to more than 50 feet and may vary in diameter from less than an inch to a couple of inches in diameter. Moreover, different cables may have different flexibilities, stiffnesses, spring tensions, obedient cable properties, tape measure material similarities, fish-tape or fish-stick similarities, push-cable similarities, etc. It is envisioned that the remote inspections device may be sold as a kit having a display housing 12, at least one imager head 14 and a set of different cables having different constructs. Additional imager heads may be included in the kit or sold individually.

Given an adaptable display housing, users may configure the inspection device to meet their particular needs. For a first task, a first type of cable attachment along with a particular image head may be selected and coupled to the display housing. For a different task, the user may detach the image head and attach an image head which provides a different function. Alternatively, the user may also need to replace the cable attachment. In this case, the user further detaches the first type of cable attachment and attaches a second type of cable attachment having a different construct than the first type of cable attachment. For example, the second type of cable attachment may have a different length, diameter, or flexibility than the first type of cable attachment. The user then selects and attaches a suitable image head to the second type of cable attachment. In this way, the more expensive display housing may be configured with different and less expensive components tailored to a particular task.

Figures 11A, 11B:
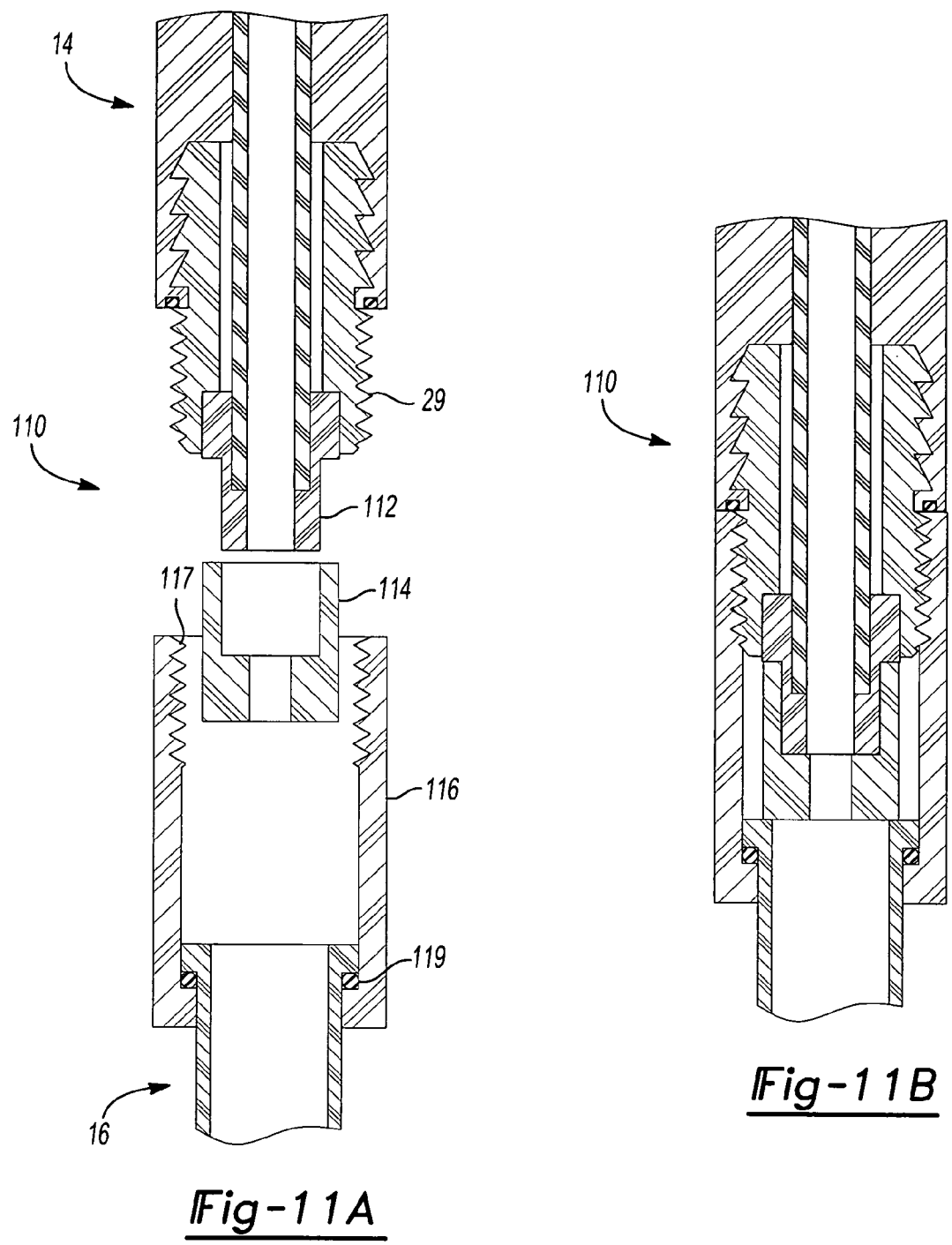
FIGS. 11A and 11B are cross-sectional view of a detachable coupling which may be used in the inspection device.

FIGS. 11A and 11B illustrate an exemplary detachable coupling 110 which may be interposed between the imager housing 14 and the flexible cable 16. On the camera side, a cylindrical sleeve 29 having an outer threaded portion protrudes from the housing. A male connector 112 is fixed within an axial passageway of the threaded sleeve. The male connector 112 is in turn electrically connected via the applicable wires to the imaging device and light sources. On the other hand, a corresponding female connector 114 is coupled to the distal end of the flexible cable 16. Likewise, the female connector 114 is electrically connected to wires which extend through the flexible cable 16 to the display housing. By plugging the male connector 112 into the female connector 114, the imager housing 14 is electrically connected to the flexible cable 16.

To provide a sealed coupling, a cylindrical coupling 116 is also disposed on the distal end of the flexible cable 16. The cylindrical coupling 116 further provides an internal grooved portion 117 which mates with the threaded portion of the sleeve on the imager housing. To complete the coupling, the cylindrical coupling 116 is slid over the female connector and screwed onto the threaded portion of the sleeve, thereby encasing the electrical connection within the coupling. An O-ring 119 or other sealing component is preferably disposed between the inner surface of the cylindrical coupling and the outer surface of the flexible cable. A detachable coupling having a similar construction may be interposed between flexible cable and the display housing. Moreover, it is envisioned that other types of detachable couplings may be employed to achieve the modularity.

Figure 12:
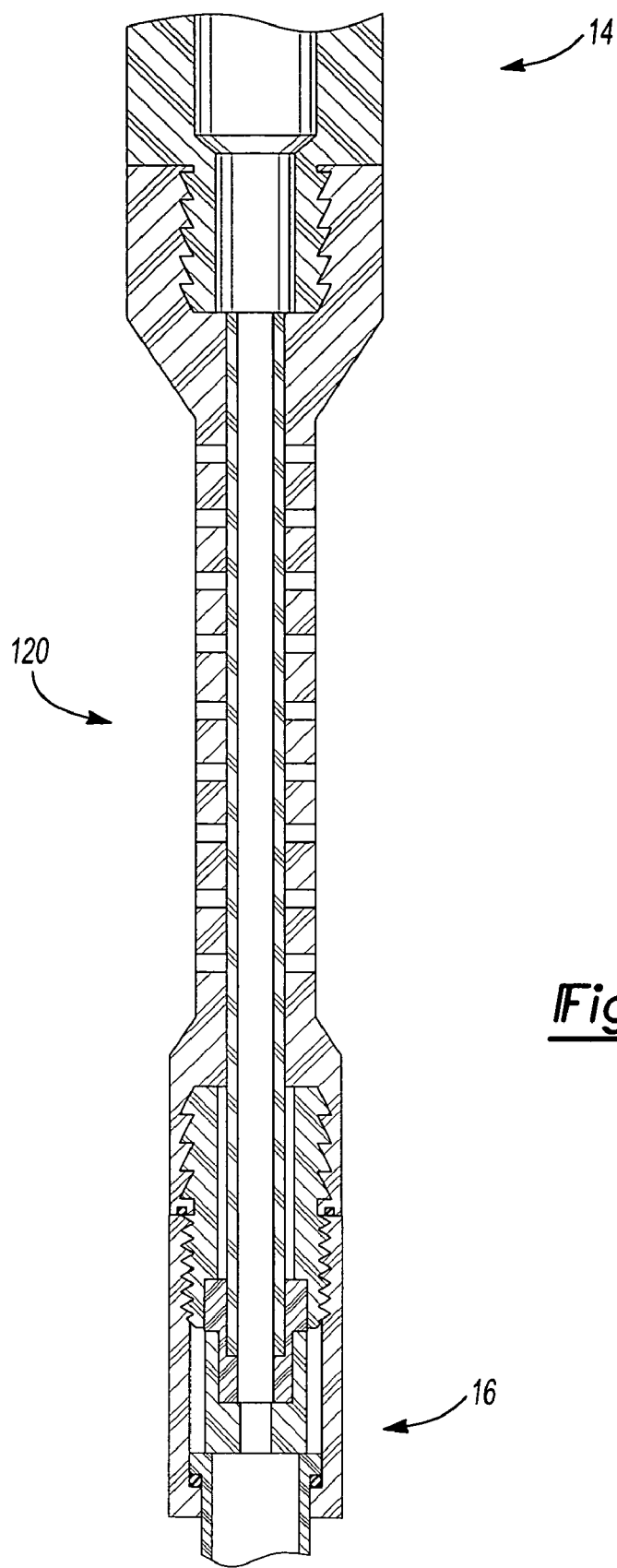
FIG. 12 is a cross-sectional view of a secondary connector which may be used with the inspection device.

In an alternative embodiment, a secondary connector 120 may be interposed between the imager housing 14 and the flexible cable 16 as shown in FIG. 12. The secondary connector 120 is designed to be more flexible than the flexible cable, thereby providing strain relief as the imager housing is snaked into an inspection area. In the exemplary embodiment, a corrugated outer surface of the secondary connector 120 provides its flexibility. On the camera side, a cylindrical sleeve having an outer threaded portion protrudes from the housing. In an exemplary embodiment, one end of the secondary connector 120 is overmolded around the cylindrical sleeve to form a coupling between the image housing 14 and the secondary connector. The other side of the secondary connector can be constructed in manner described above for coupling to the flexible cable. Again, this type of secondary connector may also be interposed between the other end of the flexible cable and the display housing.

Figure 13:
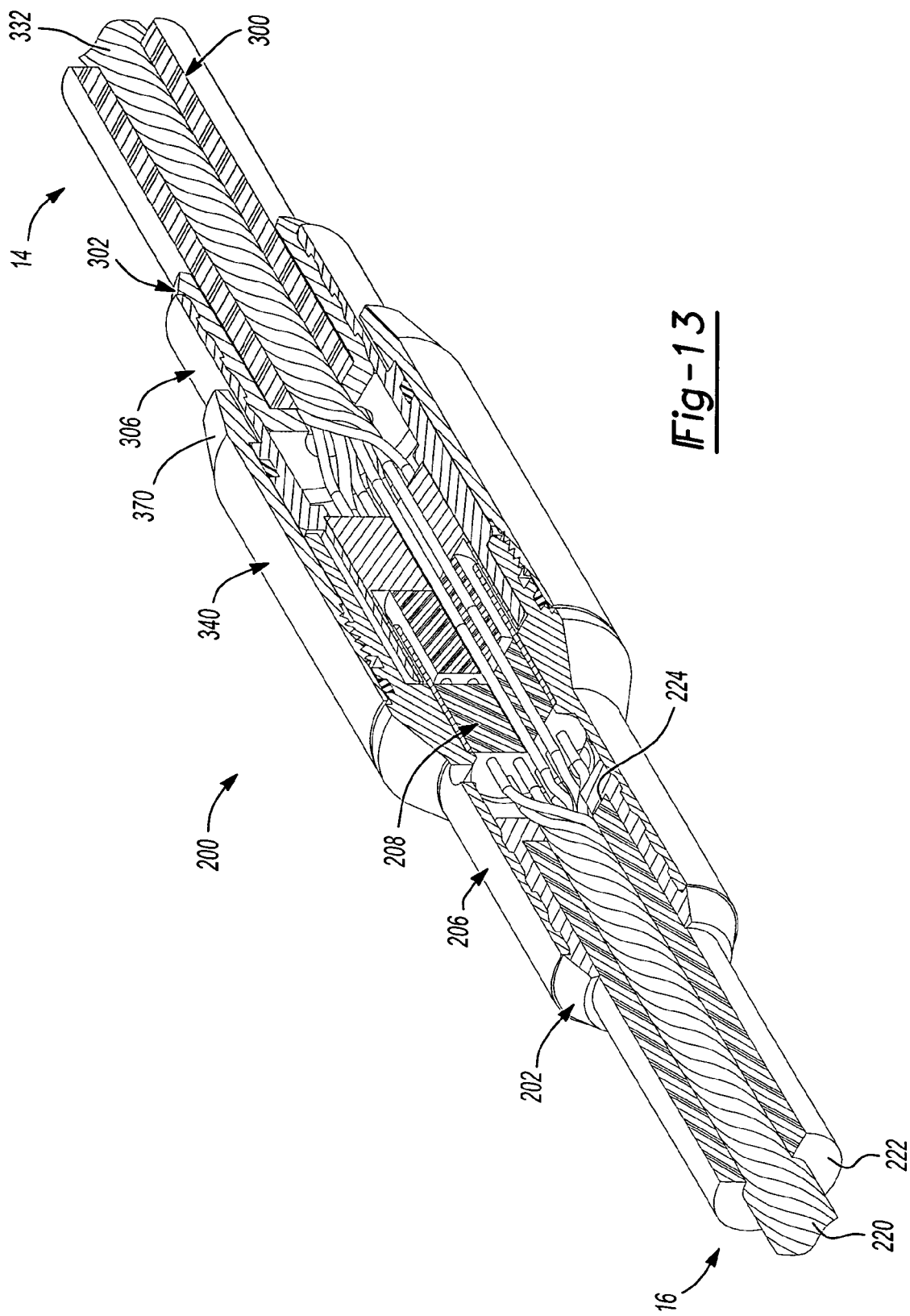
FIG. 13 is a perspective view of another exemplary detachable coupling.
Figure 14A:
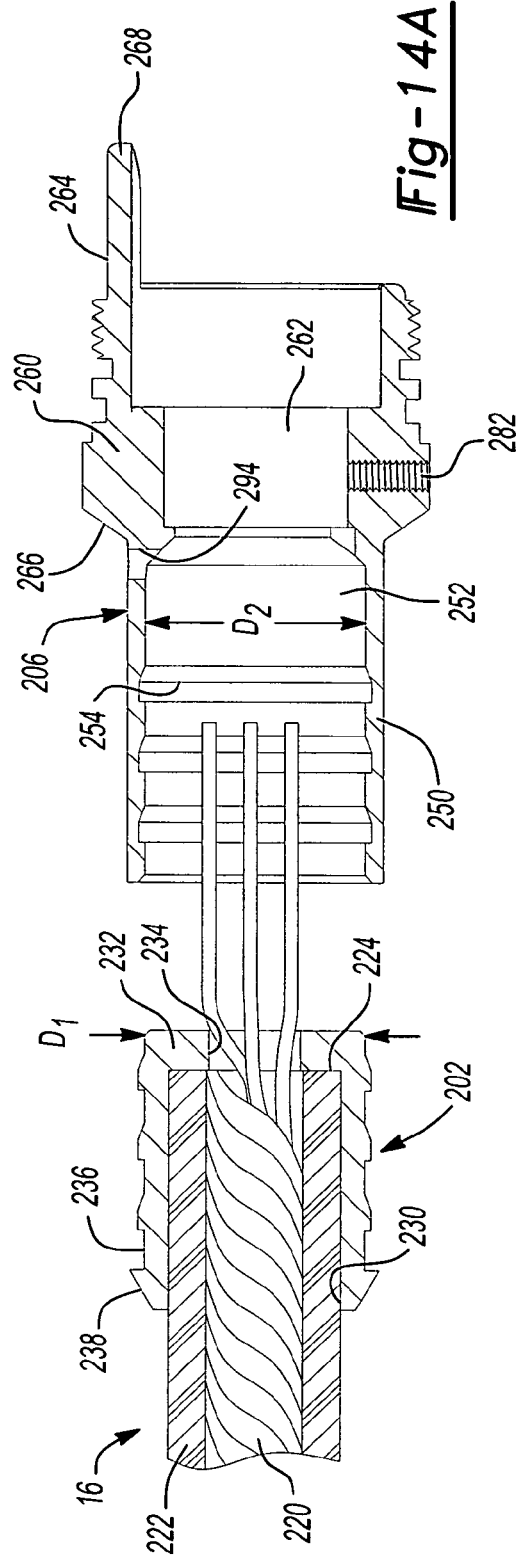
FIGS. 14A-14F are cross sectional views illustrating the assembly process for the detachable coupling.
Figure 14B:
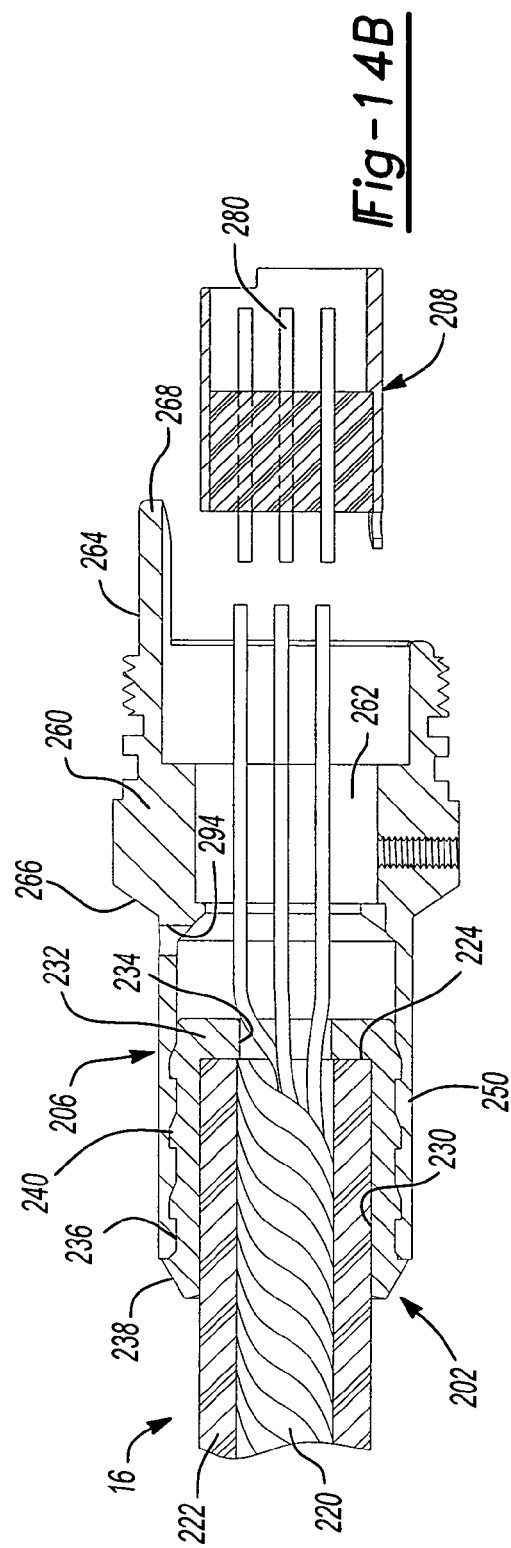
Figure 14C:
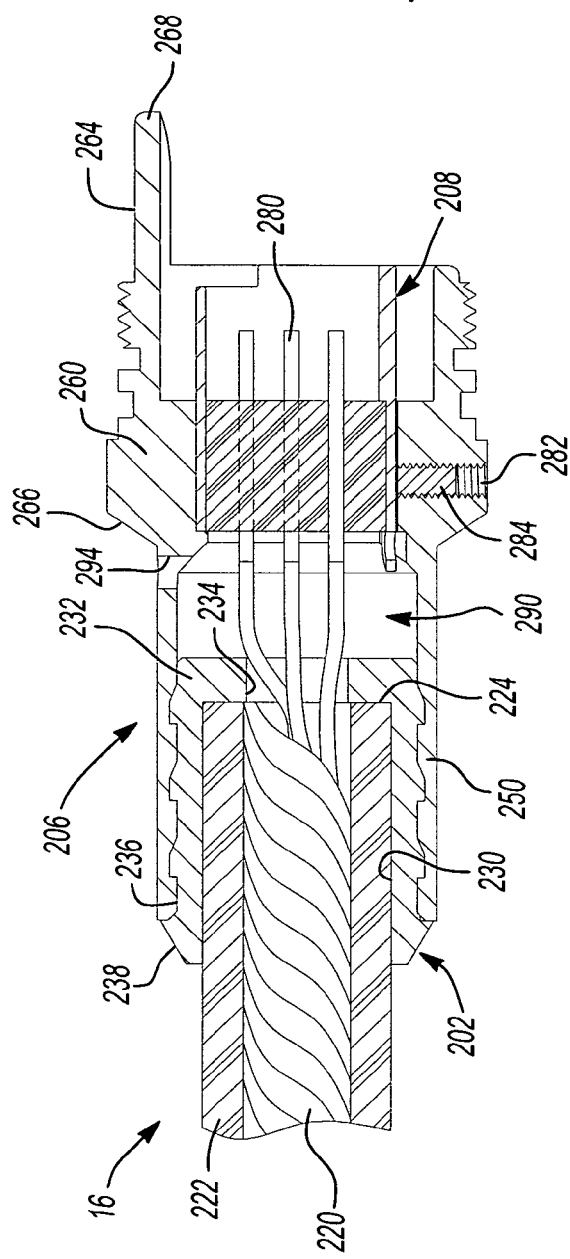
Figure 14D:
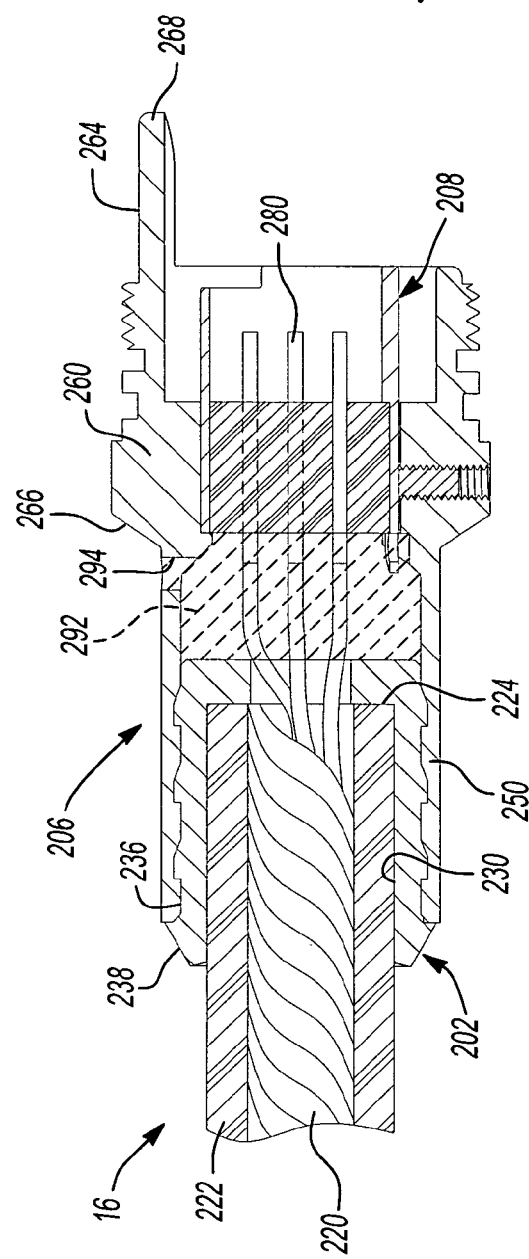
Figure 14E:
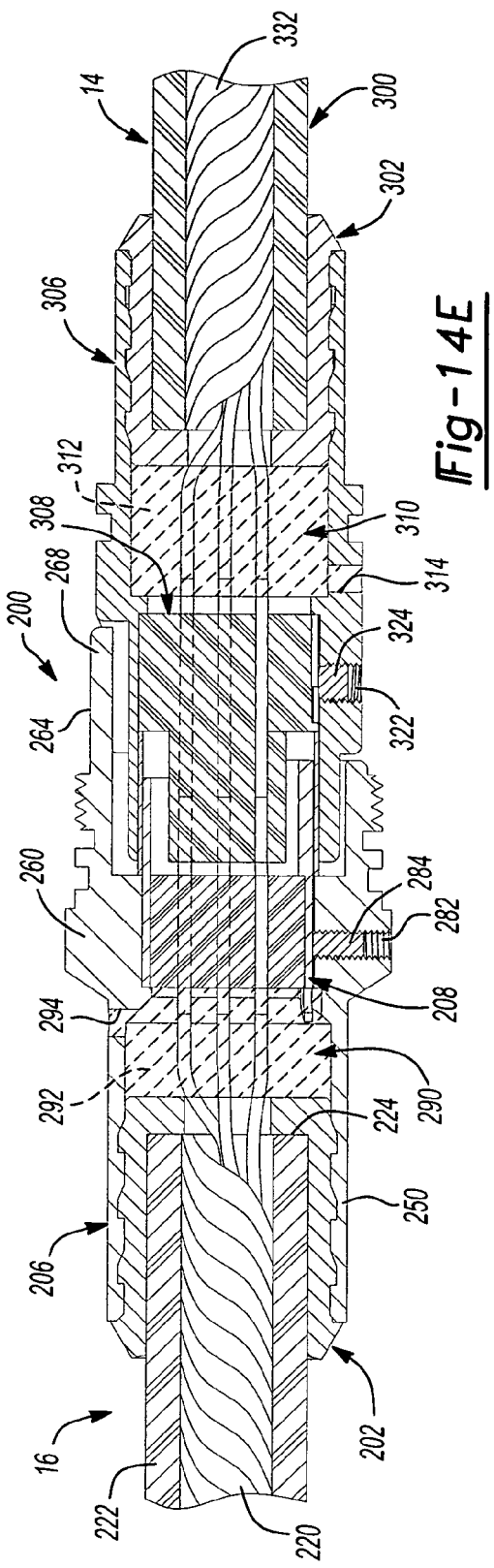
Figure 14F:
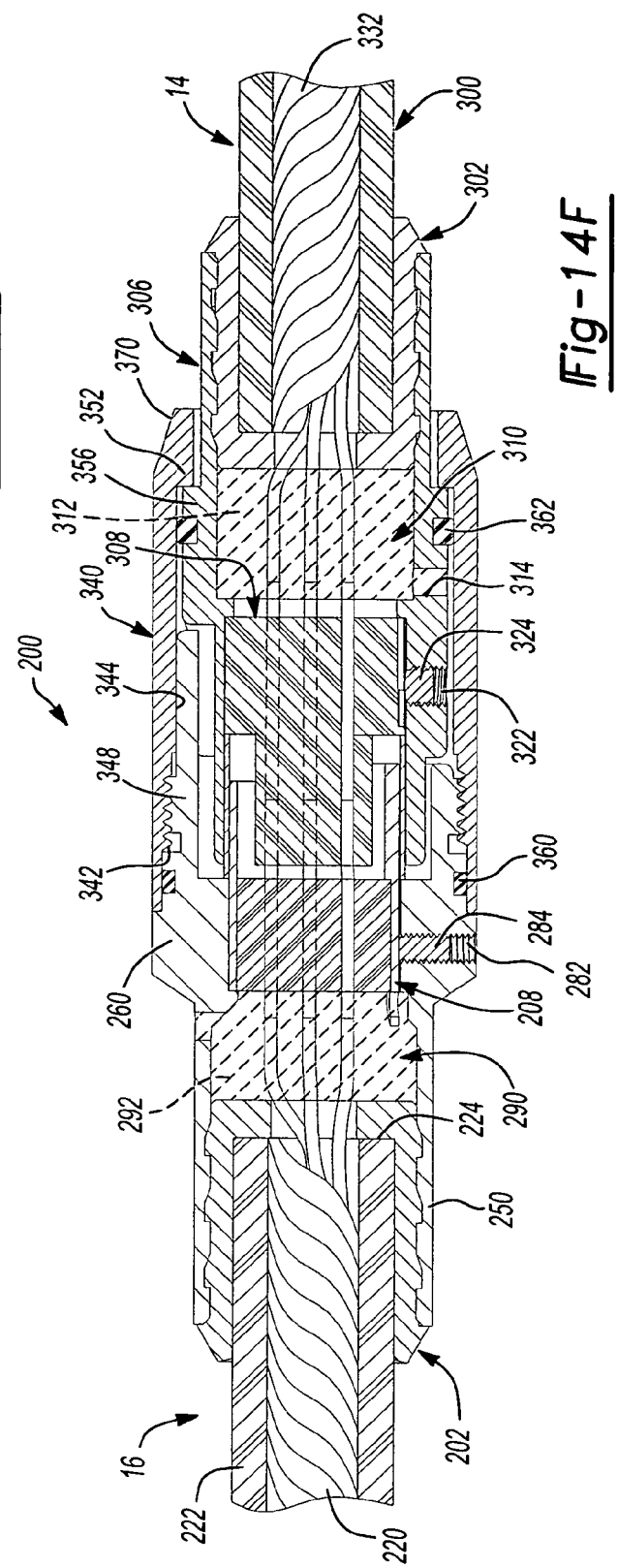
Figure 15:
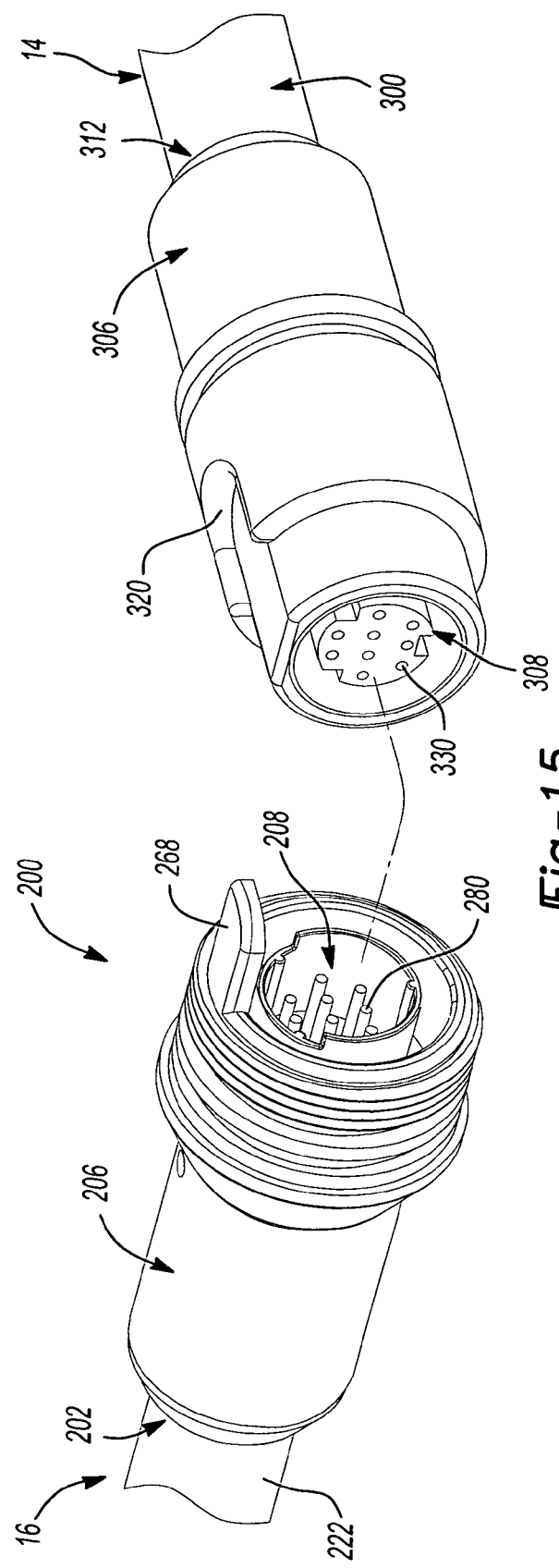
FIG. 15 is a perspective view of the detachable coupling.

FIGS. 13-15 illustrate another exemplary detachable coupling 200 and the assembly thereof. According to the principles of the present disclosure, coupling 200 may be used to interconnect different components of inspection device 10. By way of non-limiting example, coupling 200 can attach imager housing 14 and flexible cable 16 as illustrated.

In this exemplary illustration of flexible cable 16, wires 220 are covered by an outer jacket 222, and an end 224 is defined. It should be understood that, according to the principles of the present disclosure, flexible cable 16 can have a variety of components and configurations.

With particular reference to FIGS. 14A-14D, coupling 200 includes a deformable ferrule or ferrule component 202, an exterior metal connector or casing 206, and an electrical connector 208 in a first assembly of components associated with flexible cable 16. It is to be understood that, according to the principles of the present disclosure, coupling 200 and the components thereof (e.g. ferrule components, casings, and electrical connectors) can vary in many ways. Accordingly, it should be understood that the descriptions herein of coupling 200 and the components thereof are exemplary in nature.

Exemplary ferrule 202 has a generally annular shape and is disposed around flexible cable 16 with an inside surface 230 engaging outer jacket 222. Ferrule 202 further includes an end cap 232 engaged with end 224 of flexible cable 16. Wires 220 extend through an aperture 234 in end cap 232. End cap 232 provides for a fixed position of ferrule 202 along the length of flexible cable 16. Furthermore, end cap 232 provides for simple assembly of ferrule 202 and flexible cable 16, as ferrule 202 is disposed on flexible cable 16 until end 224 engages end cap 232.

Additionally, ferrule 202 includes an outside surface 236 configured to engage with casing 206. Outside surface 236 can have a diameter D1 sized to provide an interference fit with casing 206, as explained in more detail herein. Ferrule 202 also has a sloped end surface 238 at the end thereof opposite end cap 232. As explained in more detail herein, sloped end surface 238 helps facilitate the movement of coupling 200 through confined spaces. Furthermore, ferrule 202 has protrusions 240 extending from outside surface 236. As illustrated in the Figures, protrusions 240 can be in the form of ridges or splines extending around outer surface 236. As explained in more detail herein, protrusions 240 engage with complementary features of casing 206 to prevent relative axial movement therebetween. As used herein, the term "axial movement" refers to movement along the length of components of coupling 200.

Ferrule 202 is preferably comprised of an electrically insulating material such as plastic or nylon. As explained herein, in combination with other components of coupling 200, ferrule 202 electrically isolates coupling 200 from flexible cable 16 and, thus, the remainder of inspection device 10. Furthermore, as a diameter D1 of outside surface 236 can be sized to provide an interference fit with casing 206, ferrule 202 can be made of a deformable material.

Exemplary casing 206 includes a cylindrical portion 250 which is disposed over ferrule 202 and flexible cable 16. Cylindrical portion 250 of casing 206 and ferrule 202 have a sealed engagement to prevent fluid communication therebetween (e.g., to provide a watertight seal). The engagement of ferrule 202 and cylindrical portion 250 also provide a sealed engagement between ferrule 202 and flexible cable 16. Therefore, coupling 200 is watertight between flexible cable 16 and cylindrical portion 250 of casing 206. For example, ferrule 202 can be press fit into cylindrical portion 250, as an inside surface 252 of cylindrical portion 250 can have a diameter D2 smaller than the diameter D1 of a complementary portion of outside surface 236 of ferrule 202. As such, casing 206 can deform ferrule 202. Furthermore, casing 206 has a plurality of recesses 254 formed in inside surface 252 complementary to protrusions 240. Ferrule 202 is swaged into casing 206 so that protrusions 240 extend into recesses 254. The engagement of protrusions 240 and recesses 254 prevent relative axial movement between ferrule 202 and casing 206. As illustrated in the Figures, recesses 254 can be in the form of grooves extending around inside surface 252.

Casing 206 further includes a main portion 260 having an inside surface 262 and an outside surface 264. As described in more detail herein, inside surface 262 is configured to support electrical connector 208. Furthermore, as explained in more detail herein, a sloped portion 266 of outside surface 264 helps facilitate the movement of coupling 200 through confined spaces. Main portion 260 also has a tab 268 extending therefrom. Tab 268 is configured to prevent relative rotation within coupling 200, as explained in more detail herein.

Exemplary electrical connector 208 is disposed within casing 206 and supported by inside surface 262. For example, electrical connector 208 can be sized to have an interference fit with a portion of inside surface 262 to hold electrical connector 208 in place during assembly. Prongs 280 extend from electrical connector 208 and are electrically connected to wires 220. For example, wires 220 are soldered to electrical connector 208. Furthermore, electrical connector 208 isolates wires 220 and prongs 280 from casing 206. It should be understood that electrical connector 208 can have a variety of components and configurations and can be connected to wires 220 in a variety of ways.

Additionally, exemplary casing 206 can include a tap 282 proximate electrical connector 208. Referring to FIGS. 14C-14D, a set screw 284 is disposed within tap 282. Set screw 284 is tightened to engage electrical connector 208 and to help secure electrical connector 208 relative to casing 206.

With particular reference to FIG. 14C, a space 290 is defined within casing 206 and between ferrule 202 and electrical connector 208 as these components are assembled together. Wires 220 extend through space 290 from end 224 of flexible cable 16 to electrical connector 208. Referring to FIG. 14D, space 290 can be filled or backpotted with an insulating or backpotting material 292. Casing 206 includes an aperture 294 in communication with space 290. Set screw 284 engages electrical connector 208 to hold electrical connector 208 in place, and insulating material 292 is inserted through aperture 294 and fills space 290.

Insulating material 292 reduces and/or eliminates the airspace between ferrule 202 and electrical connector 208. Insulating material 292 electrically isolates the wires 220 extending through space 290 from casing 206 and serves as an adhesive to help hold electrical connector 208 in place. Furthermore, insulating material 292 increases the waterproofing, vibration resistance, and durability of coupling 200. According to the principles of the present disclosure, insulating material 292 can be made of a variety of materials. By way of non-limiting example, insulating material 292 can be a foam, epoxy, or glue. As such, insulating material 292 can be configured to harden in space 290.

With particular reference to FIGS. 14E, 14F, and 15, coupling 200 can have a second assembly of components associated with a cable segment 300 of imager housing 14 similar to the first assembly of components associated with flexible cable 16. Accordingly, it should be understood that the descriptions herein equally apply to similar components, unless otherwise noted.

Coupling 200 has a ferrule 302 engaged with cable segment 300, a casing 306 disposed over ferrule 302, and an electrical connector 308 supported within casing 306 in the second assembly of components. A space 310 is defined within casing 306 and between ferrule 302 and electrical connector 308. Space 310 is filled with insulating material 312 through a aperture 314 in casing 306.

In contrast to casing 206 of the first assembly of coupling 200, casing 306 does not include a tab extending therefrom. Rather, as shown in FIG. 15, casing 306 has a recess 320 formed therein. Recess 320 is complementary to tab 268 of casing 206 and receives tab 268 when the two assemblies of coupling 200 are mated together. With tab 268 disposed in recess 320, casings 206, 306 are inhibited from rotating relative to one another. This connection provides for torque resistance within the coupling 200.

Casing 306 also includes a threaded tap 322 and a set screw 324 disposed within tap 322. Similar to tap 282 and set screw 324 described herein, tap 322 is proximate electrical connector 308, and set screw 324 is tightened to engage electrical connector 308 and to help secure electrical connector 308 relative to casing 306.

Electrical connector 308 includes holes 330 formed herein. Holes 330 are electrically connected to wires 332 of cable segment 300. Holes 330 have a complementary size and configuration to prongs 280 of electrical connector 208. Holes 330 receive prongs 280 when the two assemblies of coupling 200 are mated together. Thereby, wires 220 of flexible cable 16 and wires 332 of cable segment 300 are electrically connected. Furthermore, the ferrules, electrical connectors, and insulating material together electrically isolate casings 206, 306 from the wires and, therefore, the rest of inspection device 10.

Both wires 220 of flexible cable 16 and wires 332 of cable segment 300 are coiled together. This configuration provides flexibility to the length of the electrical connection. Therefore, when flexible cable 16 or cable segment 300 is bent during use, or otherwise when a variation in connection length is needed during assembly, both wires 220 and 332 can accommodate a variety of connection lengths.

With particular reference to FIGS. 13 and 14F, coupling 200 further includes a sleeve 340 disposed over and engaged with casings 206, 306. In particular, a threaded portion 342 on an inside surface 344 of sleeve 340 engages a complementary threaded portion 348 on outside surface 236 of casing 206. Furthermore, a shoulder 352 on inside surface 344 of sleeve 340 engages a complementary shoulder 356 in casing 306. Therefore, sleeve 340 can be tightened onto casing 206 while engaging casing 306 to secure the two assemblies of coupling 200 together.

Sleeve 340 can also have sealed engagements with casings 206, 306. In particular, a first sealing member 360 is supported by casing 206 and engages inside surface 344 of sleeve 340. Additionally, a second sealing member 362 is supported by casing 306 and also engages inside surface 344 of sleeve 340. These sealed engagements between casings 206, 306 and sleeve 340, together with the engagements between the casings and the ferrules and the ferrules and the cables, make coupling 200 watertight.

Sleeve 340 further includes a sloped surface 370 proximate an end thereof. Sloped surface 370, together with sloped portion 266 of outside surface 264 of casing 206 and with the sloped surfaces of the ferrules, facilitates the movement of coupling 200 through confined spaces. For example, if the coupling 200 is maneuvering through a confined space such as an angled plumbing fitting, the sloped surfaces inhibit coupling 200 from engaging an edge or other protrusion in a manner which would impede or prevent further travel of coupling 200.

Coupling 200 can vary in many ways. The components thereof can have a variety of configurations and can include a variety of materials. Accordingly, it should be understood that the description of coupling 200 herein is exemplary in nature.

Figure 16A:
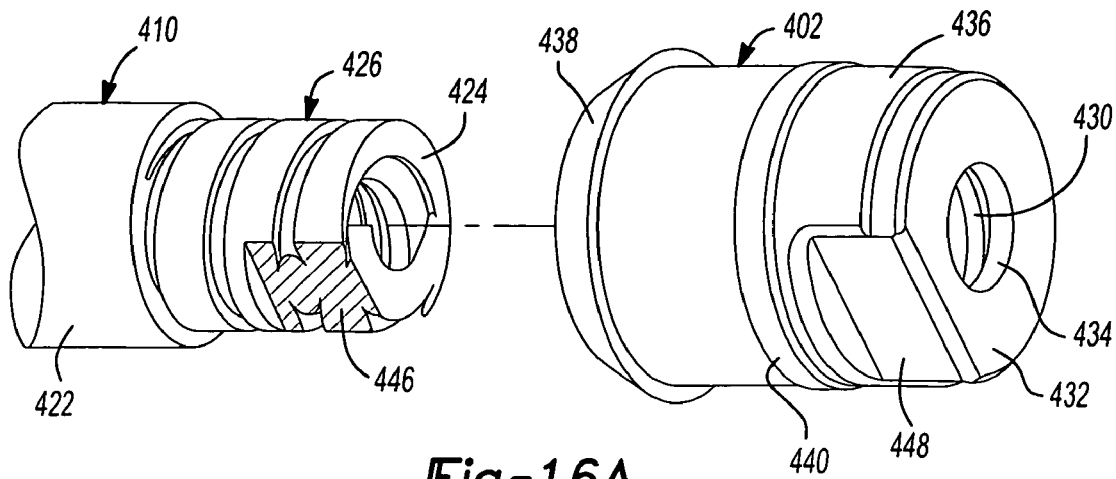
FIGS. 16A-16B are perspective views of a portion of another exemplary detachable coupling.
Figure 16B:
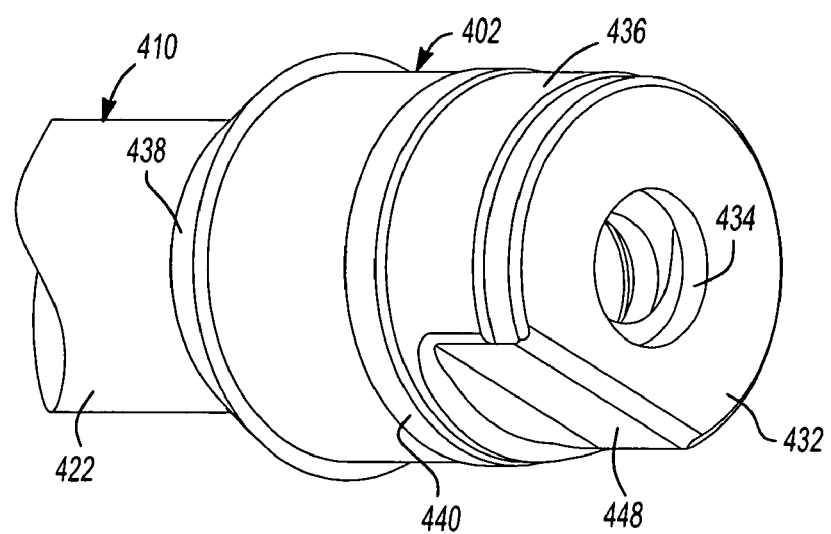
Figure 17:
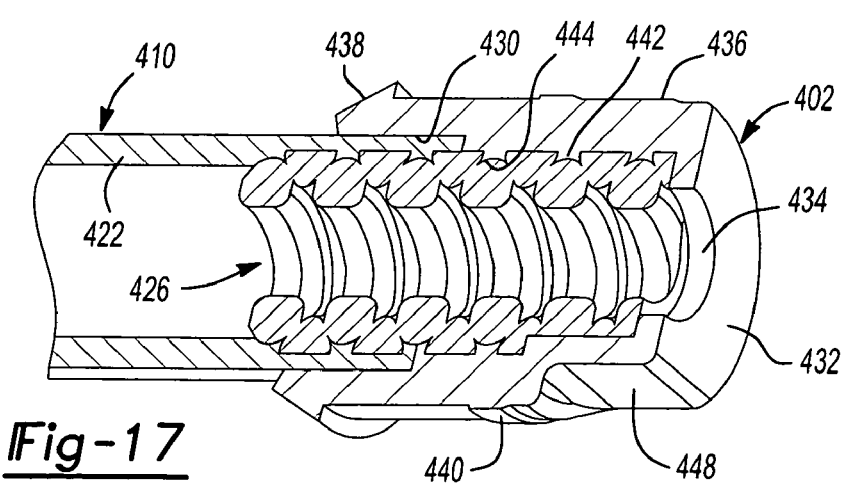
FIG. 17 is a cross sectional view illustrating the portion of the detachable coupling of FIG. 16B.

Referring to FIGS. 16-17, another exemplary deformable ferrule or ferrule component 402 is illustrated. It should be understood that ferrule 402 can be included in a coupling according to the principles of the present disclosure such as is described herein with regard to ferrules 202, 302.

Ferrule 402 is disposed over a cable 410. Cable 410 has an outer jacket 422. Outer jacket 422 does not extend to an end 424 of cable 410. As such, an inner component 426 is exposed. Furthermore, wires (not shown) can extend through cable 410. Ferrule 402 has a generally annular shape and is disposed around cable 410 with an inside surface 430 engaging outer jacket 422 and inner component 426. Ferrule 402 further includes an end cap 432 engaged with end 424. An aperture 434 is provided in end cap 432 so that wires (not shown) of cable 410 can extend therethrough.

Ferrule 402 also includes an outside surface 436. Outside surface 436 is configured to engage with a casing component in a similar way as described herein with respect to ferrules 202, 302. Ferrule 402 also has a sloped end surface 438 at the end thereof opposite end cap 432. As explained herein, such sloped surfaces help facilitate movement through confined spaces. Additionally, ferrule 402 has a single protrusion 440 extending from outside surface 436. Similar to protrusions 240 of ferrule 202 described herein, protrusion 440 engages with a complementary feature of a casing or similar component to prevent relative axial movement therebetween. As illustrated in the Figures, protrusion 440 can be in the form of a ridge or spline extending around outer surface 436.

Ferrule 402 is overmolded onto cable 410. In particular, ferrule 402 is molded into shape over cable 410 so that a portion of inside surface 430 engages outer jacket 422 and another portion of inside surface 430 engages inner component 426 with projections 442 extending from inside surface 430 into grooves 444 of inner component 426. Therefore, ferrule 402 and cable 410 have a sealed engagement which inhibits fluid communication therebetween. Ferrule 402 is also secured along to the axial direction of cable 410. Furthermore, ferrule 402 is formed with a key portion 446 complementary to a key portion 448 of inner component 426. The key portions engage and inhibit relative rotation of ferrule 402 and inner component 426. As such, the key portions inhibit the effects of rotational torque on the assembly.

It should be understood that ferrule 402 can otherwise be similar ferrules 202, 302 described herein. For example, ferrule 402 can be comprised of an insulating material such as plastic or nylon. Furthermore, ferrule 402 can be a deformable material. As such, ferrule 402 can be sized so as to provide an interference fit with a casing or similar component. Additionally, a casing or similar component can be disposed over and engaged with ferrule 402 such that ferrule 402 provides a seal between cable 410 and the casing or similar component and such that ferrule 402 electrically isolates cable 410 and the casing or similar component.

What is claimed is:

1. A detachable coupling for selectively attaching first and second cables of a remote inspection device, the detachable coupling comprising:

a first ferrule component provided over the first cable and encasing an end of the first cable, said first ferrule component being an electrical insulator;

a first casing engaging said first ferrule component, said first casing and said first ferrule component being secured to the first cable, said first ferrule component electrically isolating said first casing from the first cable;

a first electrical connector supported within said first casing and electrically connected to wires in the first cable;

a second ferrule component provided over the second cable and encasing an end of the second cable, said second ferrule component being an electrical insulator;

a second casing engaging said second ferrule component, said second casing and said second ferrule component being secured to the second cable, said second ferrule component electrically isolating said second casing from the second cable; and a second electrical connector supported within said second casing and electrically connected to wires in the second cable, wherein said first and second electrical connectors engage and electrically connect the wires of the first and second cables, wherein said first and second ferrule components each have at least one protrusion extending from an outer surface thereof, said first and second casings each have at least one recess formed in an inner surface thereof, said at least one protrusion of said first ferrule component extending into said at least one recess of said first casing and said at least one protrusion of said second ferrule component extending into said at least one recess of said second casing so as to inhibit relative axial movement therebetween.

2. A detachable coupling for selectively attaching first and second cables of a remote inspection device, comprising:

a first casing having a first longitudinal axis and a passage extending between opposing ends of said first casing along said first longitudinal axis, said passage having a first portion adjacent to one end of said first casing defining a first ferrule socket and a second portion adjacent to the opposite end of said first casing defining a first connector socket;

a first ferrule component comprised of an electrical insulating material and encasing an end of the first cable, wherein said first ferrule component is inserted into the first ferrule socket and electrically isolates said first cable from said first casing;

a first electrical connector is electrically connected to wires of the first cable and inserted into said first connector socket;

a second casing having a second longitudinal axis and a second passage extending between opposing ends of said second casing along said second longitudinal axis, said second passage having a first portion adjacent to one end of said second casing defining a second ferrule socket and a second portion adjacent to the opposite end of said second casing defining a second connector socket;

a second ferrule component comprised of an electrical insulating material and encasing an end of the second cable, wherein said second ferrule component is inserted into said second ferrule socket and electrically isolates said second cable from the second casing; and a second electrical connector electrically connected to wires of the second cable and inserted into said second connector socket.

3. The detachable coupling of claim 2 wherein said detachable coupling further includes a sleeve overlapping said first and second casings.

4. The detachable coupling of claim 3 wherein said detachable coupling further includes a first sealing element disposed between said sleeve and said first casing and a second sealing element disposed between said sleeve and said second casing.

5. The detachable coupling of claim 2 further comprising an electrically insulating potting material injected into each of said first and second casings, where the potting material is disposed between an inward facing end of the first and second ferrule components and said first and second electrical connectors, respectively.

6. The detachable coupling of claim 2 wherein one of said first and second casings has a tab portion extending therefrom and the other of said first and second casings having a recess portion complementary to said tab portion, said tab portion engaging said recess portion to inhibit relative rotation between said first and second casings.

7. The detachable coupling of claim 1 wherein said first and second ferrule components each have a sloped end surface angled from the first and second casings toward the first and second cables, respectively.

8. The detachable coupling of claim 2 wherein the first ferrule component having a hollow cylindrical shape that encases the end of the first cable.

9. The detachable coupling of claim 2 wherein the first ferrule component extends longitudinally along the first longitudinal axis of the first casing and beyond the end of the first casing.

10. A coupling for interconnecting components of a remote inspection device, comprising:

a cable for interconnecting the components of the remote inspection device; and a first assembly attached to one end of the cable and including:

a first casing having a passage extending between opposing ends of said first casing along a longitudinal axis, said passage having a first portion adjacent to one end of said first casing defining a ferrule socket and a second portion adjacent to the opposite end of said first casing defining a connector socket;

a first ferrule component having a hollow cylindrical body comprised of an electrical insulating material and with at least one protrusion formed on a radial exterior surface of the cylindrical body, wherein the end of the cable is inserted into the first ferrule component and the first ferrule component is inserted into the first ferrule socket, thereby electrically isolating the cable from the first casing;

a first electrical connector is electrically connected to wires of the first cable and inserted into said first connector socket.

11. The coupling of claim 10 where first casing having a recess formed on an inner surface of the first ferrule socket such that the protrusion on the first ferrule component extends into the recess and inhibits axial movement therebetween.

12. The coupling of claim 10 further comprises an electrically insulating potting material injected into the first casing between an inward facing end of the first ferrule component and said first electrical connector.

13. The coupling of claim 10 wherein the first ferrule component encases the end of the cable without encapsulating an end face of the cable.

14. The coupling of claim 10 wherein the first ferrule component extends longitudinally along the first longitudinal axis of the first casing and beyond the end of the first casing.

15. The coupling of claim 10 wherein a portion of said outer surface of said first ferrule component defines an outer diameter and a complementary portion of the first ferrule component socket defines a diameter smaller than the outer diameter such that the first casing deforms the first ferrule component at said portion of said outer surface.

16. A remote inspection device, comprising:

an imager housing including an imaging device;

a display housing including a display device and a portable power source;

a cable having a first end coupled to said imager housing and a second end detachably coupled via a coupling to said display housing, said cable having a plurality of wires and an outer jacket, said wires operably connecting said imaging device, said display device and said portable power source; and said coupling including a first assembly fixed to said second end of said cable and a second assembly coupled to said display housing, said first assembly including:
- a first casing having a first longitudinal axis and a passage extending between opposing ends of said first casing along said first longitudinal axis, said passage having a first portion adjacent to one end of said first casing defining a first ferrule socket and a second portion adjacent to the opposite end of said first casing defining a first connector socket;
- a first ferrule component comprised of an electrical insulating material and encasing an end of the cable, wherein said first ferrule component is inserted into the first ferrule socket and electrically isolates said cable from said first casing;
  - a first electrical connector is electrically connected to the plurality of wires of the cable and inserted into said first connector socket.

17. The coupling of claim 16 further comprises an electrically insulating potting material injected into the first casing between an inward facing end of the first ferrule component and said first electrical connector.

18. The coupling of claim 16 wherein the first ferrule component having a hollow cylindrical shape.

19. The coupling of claim 18 wherein cylindrical body having at least one protrusion formed on a radial exterior surface thereof and the first casing having a recess formed on an inner surface of the first ferrule socket such that the protrusion on the first ferrule component extends into the recess and inhibits axial movement therebetween.

20. The coupling of claim 16 wherein the first ferrule component extends longitudinally along the first longitudinal axis of the first casing and beyond the end of the first casing.

* * * * *